US012044658B2

(12) United States Patent
Kobayashi et al.

(10) Patent No.: US 12,044,658 B2
(45) Date of Patent: Jul. 23, 2024

(54) MOVING INSPECTION DEVICE, MOVING INSPECTION METHOD, AND METHOD FOR MANUFACTURING STEEL MATERIAL

(71) Applicant: JFE STEEL CORPORATION, Tokyo (JP)

(72) Inventors: Masaki Kobayashi, Tokyo (JP); Koji Yamashita, Tokyo (JP); Kouyou Miyawaki, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 238 days.

(21) Appl. No.: 17/640,984

(22) PCT Filed: Sep. 15, 2020

(86) PCT No.: PCT/JP2020/034855
§ 371 (c)(1),
(2) Date: Mar. 7, 2022

(87) PCT Pub. No.: WO2021/054314
PCT Pub. Date: Mar. 25, 2021

(65) Prior Publication Data
US 2022/0341884 A1    Oct. 27, 2022

(30) Foreign Application Priority Data
Sep. 19, 2019   (JP) .................. 2019-170645

(51) Int. Cl.
*G01N 29/265* (2006.01)
*G01N 29/24* (2006.01)
*G01N 33/20* (2019.01)

(52) U.S. Cl.
CPC ....... *G01N 29/265* (2013.01); *G01N 29/2493* (2013.01); *G01N 33/20* (2013.01)

(58) Field of Classification Search
CPC .. G01N 29/265; G01N 29/2493; G01N 33/20; G01N 29/221; G01N 29/043;
(Continued)

(56) References Cited

U.S. PATENT DOCUMENTS

| 8,511,164 B2 | 8/2013 | Klee et al. |
| 9,310,319 B2 | 4/2016 | Sato et al. |

(Continued)

FOREIGN PATENT DOCUMENTS

| CN | 101545975 A | 9/2009 |
| CN | 104535651 A | 4/2015 |

(Continued)

OTHER PUBLICATIONS

Aug. 16, 2023 Office Action issued in Chinese Patent Application No. 202080065863.0.

(Continued)

*Primary Examiner* — Jacques M Saint Surin
(74) *Attorney, Agent, or Firm* — Oliff PLC

(57) ABSTRACT

A moving inspection device inspecting an inspection target while realizing the simplification of the configuration and significant size reduction/weight reduction of the device, a moving inspection method, and a method for manufacturing a steel material. The device includes a moving inspection device body configured to inspect an inspection target for defects while moving over its surface. The moving inspection device body includes: a carriage that moves by at least two wheels that rotate forward and backward over the surface; and at least one inspection sensor on the front end side or the rear end side of the carriage. An inspection region of the inspection target is divided into two divided regions across a straight line, and the carriage is configured to move (Continued)

when the inspection sensor is directed to side edges sides of the divided regions facing the straight line in each of the two divided regions.

10 Claims, 14 Drawing Sheets

(58) Field of Classification Search
CPC ...... G01N 29/225; G01N 29/28; G01N 29/04; G01N 2291/023; G01N 2291/044; G01N 2291/263; G01N 2291/2632; G01N 2291/0289; G01N 2291/0234
USPC .......................................................... 73/620
See application file for complete search history.

(56) References Cited

U.S. PATENT DOCUMENTS

| | | | |
|---|---|---|---|
| 9,982,833 B2* | 5/2018 | Yeum | F16M 11/2085 |
| 10,031,068 B2* | 7/2018 | Ito | G01R 33/032 |
| 10,317,190 B2 | 6/2019 | Hatahori et al. | |
| 10,732,078 B2* | 8/2020 | Watanabe | H02K 15/02 |
| 11,175,240 B2* | 11/2021 | Otsuki | G01N 21/8806 |
| 11,359,942 B2* | 6/2022 | Kuwahara | G01D 11/30 |
| 2009/0178486 A1 | 7/2009 | Klee et al. | |
| 2015/0192529 A1 | 7/2015 | Sato et al. | |
| 2018/0283847 A1 | 10/2018 | Hatahori et al. | |

FOREIGN PATENT DOCUMENTS

| | | | | |
|---|---|---|---|---|
| CN | 104685970 A | 6/2015 | | |
| CN | 108760878 A | 11/2018 | | |
| CN | 108956761 A | 12/2018 | | |
| CN | 209296602 U | 8/2019 | | |
| GB | 1060816 A | 3/1967 | | |
| GB | 1114835 A | 5/1968 | | |
| JP | S60-58505 A | 4/1985 | | |
| JP | H01-137408 U | 9/1989 | | |
| JP | H02-129547 A | 5/1990 | | |
| JP | H09-49827 A | 2/1997 | | |
| JP | 2014-089173 A | 5/2014 | | |
| JP | 2015-194491 A | 11/2015 | | |
| JP | 5954241 B2 | 7/2016 | | |
| JP | 5999214 B2 | 9/2016 | | |
| RU | 2376596 C2 | 12/2009 | | |
| WO | WO-2020171090 A1 * | 8/2020 | ........... | G01N 29/041 |

OTHER PUBLICATIONS

Apr. 29, 2022 Office Action issued in Russian Patent Application No. 2022107037.
Sep. 15, 2022 Extended European Search Report issued in European Patent Application No. 20865542.3.
Dec. 8, 2020 Search Report issued in International Patent Application No. PCT/JP2020/034855.
Mar. 15, 2022 International Preliminary Report on Patentability issued in International Patent Application No. PCT/JP2020/034855.

* cited by examiner

MOVING INSPECTION DEVICE, MOVING INSPECTION METHOD, AND METHOD FOR MANUFACTURING STEEL MATERIAL

TECHNICAL FIELD

The present invention relates to a moving inspection device inspecting an inspection target for defects while moving over the surface of the inspection target, a moving inspection method, and a method for manufacturing a steel material.

BACKGROUND ART

Conventionally, in order to ensure the quality of metal plates, such as steel plates, as an inspection target, the steel plates or the like are inspected for surface defects or internal defects by ultrasonic flaw detection or the like. In the ultrasonic flaw detection, a plurality of ultrasonic flaw detection heads as inspection sensors arranged in parallel is brought into contact with a metal plate, such as a steel plate, conveyed on a feed roller of a production line via a water film, and then the metal plate is automatically inspected in on-line, for example. In off-line, the ultrasonic flaw detection heads are moved by a hand carriage or the like to be brought into contact with a stopped metal plate, such as a steel plate, via a water film, and then the metal plate is manually inspected.

In general, the ultrasonic flaw detection heads are connected to an ultrasonic flaw detector body with a flaw detection cable, outputs (results) obtained by the flaw detection by the ultrasonic flaw detection heads are input into the ultrasonic flaw detector body, and the outputs (results) are input into a data processing device to be processed, so that the metal plate is inspected for the presence or absence of internal defects. In the case of the ultrasonic flaw detection, water as a medium for passing ultrasonic waves is sprayed to an inspection surface (surface) of the metal plate, such as the steel plate, so that a water film is formed on the inspection surface (surface) of the metal plate. Therefore, when performing the ultrasonic flaw detection of the metal plate as the inspection target in off-line, the surface of the metal plate is wet with water to be slippery. The metal plate is placed on a skid or the like installed on the floor surface in many cases, and therefore an inspector moves on the wet metal plate with a level difference, which causes a risk that the inspector falls.

In order to perform highly accurate ultrasonic flaw detection, the ultrasonic flaw detection heads as the inspection sensors need to be accurately moved along a predetermined scanning line. However, a preparation to draw the scanning line on the metal plate requires time and labor and, at the same time, there is a limit to the accuracy of the manual movement of the ultrasonic flaw detection heads.

In order to eliminate such inconvenience caused by the manual operations, moving inspection devices for metal plate have been proposed in the past, and, for example, those illustrated in PTLS 1 and 2 have been proposed.

A moving inspection device for metal plate illustrated in PTL 1 is a moving inspection device for metal plate inspecting a metal plate using an indoor position measuring system performing self-position measurement in an indoor space based on the principle of triangulation. The moving inspection device for metal plate includes a carriage having: four wheels capable of rotating forward and backward; and a drive unit rotating and driving the wheels and individually and independently turning and driving the wheels, and traveling over the metal plate surface. The carriage is further mounted with a navigation signal transmitter or a navigation signal receiver constituting the indoor position measuring system and transmitting or receiving an indoor position measuring system signal and is provided with inspection sensors inspecting a metal plate for defects. The moving inspection device for metal plate includes a control means of calculating a deviation from a self position recognized using the indoor position measuring system signal and a target position, instructing the drive unit to rotate the wheels forward, rotate the wheels backward, stop the wheels, and turn each wheel according to the deviation, and causing the carriage to move laterally, obliquely, forward and backward, or turn on the spot to cause the carriage to autonomously travel to a predetermined target position.

A moving inspection device for metal plate illustrated in PTL 2 is a moving inspection device for metal plate moving over a metal plate based on information from a position measuring means and inspecting the metal plate for the presence or absence of defects present on the surface of the metal plate or inside the metal plate and including a carriage having at least two wheels capable of rotating forward and backward and a drive unit driving the wheels. The carriage is mounted with flaw detection heads each including an ultrasonic flaw detection probe inspecting the metal plate. The moving inspection device for metal plate includes a control unit calculating a deviation between the position of the inspection device recognized by the position measuring means and a target position, instructing the drive unit to rotate the wheels forward, rotate the wheels backward, and stop the wheels such that the deviation is minimized, and controlling the inspection device to autonomously travel to a predetermined target position. The control means has a function of detecting either or both of a weight change of the inspection device and sliding resistance between the metal plate and the flaw detection heads and feedbacking a correction value obtained from the detected values to the instruction.

CITATION LIST

Patent Literature

PTL 1: JP 5954241 B
PTL 2: JP 5999214 B

SUMMARY OF INVENTION

Technical Problem

However, the conventional moving inspection devices for metal plate illustrated in PTLS 1 and 2 have had the following problems.

More specifically, in both the moving inspection devices for metal plate illustrated in PTLS 1 and 2, the carriage is provided with four wheels capable of rotating forward and backward and is provided with a drive unit rotating and driving each wheel and individually and independently turning and driving each wheel.

Both the moving inspection devices for metal plate illustrated in PTLS 1 and 2 include a scanning actuator causing the flaw detection heads to scan in the horizontal direction to move the flaw detection heads to an end part position of the metal plate. In the moving inspection devices for metal plate illustrated in PTLS 1 and 2, the moving inspection device for metal plate is stopped once at a point in time when an edge detection sensor provided in the moving inspection device for metal plate detects an end part of the metal plate. Then, from that point in time, the flaw detection heads are caused to scan in the horizontal direction by the scanning actuator to move the flaw detection heads to the end part position of the metal plate, thereby performing an appropriate inspection up to the end part of the metal plate.

In such moving inspection devices for metal plate illustrated in PTLS 1 and 2, in addition to the fact that the number of wheels themselves is as large as four, the drive unit turning and driving each wheel is required, the scanning actuator itself moving the flaw detection heads is required, and further a control device controlling the scanning actuator is required.

This has posed a problem that the device configuration is complicated and the weight of the entire device significantly increases.

Therefore, the present invention has been made to solve the conventional problems. It is an object of the present invention to provide a moving inspection device capable of appropriately inspecting an inspection target while realizing the simplification of the configuration and significant size reduction/weight reduction of the device, a moving inspection method, and a method for manufacturing a steel material.

Solution to Problem

The present inventors conducted various studies to solve the above-described problems, and, as a result, have obtained the following findings.

First, FIG. 14 illustrates a typical movement route of a moving inspection device 100 performing four-wheel drive/four-wheel steering. The movement route means that a moving inspection device 100 performing four-wheel drive/four-wheel steering moves at a predetermined pitch in a rectangular inspection region of a rectangular steel plate S as an inspection target, and coincides with a center track of the moving inspection device 100. The movement route repeats linear vertical movement and linear horizontal movement, and thus the moving inspection device 100 requires four-wheel drive/four-wheel steering. Further, a scanning actuator (not illustrated) singly moving inspection sensors 101, which is described later, is required, which increases the weight of the moving inspection device.

FIG. 15 illustrates a specific movement route of the moving inspection device 100 performing four-wheel drive/four-wheel steering when inspecting the steel plate S as the inspection target by the moving inspection device 100.

The moving inspection device 100 first moves along the width direction of the steel plate S from a position where the center as viewed from the plane is located at a point P11 in a first inspection path and, simultaneously therewith, performs the inspection by the inspection sensors 101. Then, the moving inspection device 100 stops at a position where the center as viewed from the plane is located at a point P12. Thereafter, the inspection sensors 101 are moved to the side edge of the steel plate S by the scanning actuator (not illustrated) (generally a linear slider or the like) as illustrated by the broken line arrows, thereby completing the inspection of the path. Thereafter, in the first movement path, the moving inspection device 100 moves by a predetermined distance (the same distance as the inspection pitch) in the longitudinal direction of the steel plate S by turning each of the four wheels (not illustrated) 90° on the spot to reach the next inspection path. Thereafter, the inspection path and the movement path are similarly repeated, so that the inspection of the steel plate S as the inspection target is completed by the moving inspection device 100 performing four-wheel drive/four-wheel steering.

In contrast thereto, when movement other than the movement in the movement route is allowed in the inspection of the steel plate S by a moving inspection device, it is not necessary to use the four-wheel drive/four-wheel steering as a wheel drive mechanism. In order to realize the simplification of the device configuration and significant size reduction/weight reduction of the moving inspection device, the present inventors have found that the steel plate S can be inspected by a moving inspection device using the drive of at least two wheels capable of rotating forward and backward, not turning each wheel, and not requiring the scanning actuator causing the inspection sensors to scan.

In order to inspect the steel plate S by such a moving inspection device, first, a rectangular inspection region of a surface Sa of the rectangular steel plate S as the inspection target is divided into two divided regions of a divided region A1 and a divided region A2 across the center line (straight line) in the width direction of the steel plate S as illustrated in FIG. 16.

As illustrated in FIG. 17, when the steel plate S is inspected, a carriage 31 of a moving inspection device body 30 is moved in a state where flaw detection heads 44 as inspection sensors are directed to side edges A1a, A2a sides of the divided regions A1, A2 facing the above-described center line (straight line) in each of the two divided regions A1, A2, respectively.

A movement route of the moving inspection device body 30 when inspecting the steel plate S is briefly described with reference to FIG. 17. First, in the divided region A1 of a front half, the moving inspection device body 30 moves along the width direction of the steel plate S from a position where the center as viewed from the plane of the moving inspection device body 30 with the flaw detection heads 44 located on the center line (straight line) is located at a point P1 in a first inspection path and, simultaneously therewith, performs the inspection with the flaw detection heads 44. Then, the moving inspection device body 30 stops at a position where the center as viewed from the plane of the moving inspection device body 30 with the flaw detection heads 44 located at the side edge A1a of the divided region A1 is located at a point P2. Hence, the flaw detection heads 44 are located at the side edge A1a of the divided region A1, and therefore a scanning actuator for moving the flaw detection heads 44 to the side edge A1a of the divided region A1 is not required.

Then, in the first movement path, two wheels 32 provided on both the right and left sides (both sides in the longitudinal direction of the steel plate S) of the carriage 31 of the moving inspection device body 30 are rotated backward while giving a right/left rotational speed difference to the right and left wheels 32. Thus, the center as viewed from the plane of the moving inspection device body 30 moves from the point P2 to a point P3 in a track containing two curves R1, R2, and then the moving inspection device body 30 stops. The point P3 is a point where the flaw detection heads 44 are located at the other positions on the center line (straight line) (positions where the flaw detection heads 44 are shifted by a predetermined distance (corresponding to an inspection pitch D) in the longitudinal direction of the steel plate S with respect to the initial positions of the flaw detection heads 44). The point P3 is a starting point for the next inspection path. The interval between the points 1 and 3 is the inspection pitch D.

Thereafter, the inspection path and the movement path are similarly repeated, so that the inspection in the divided region A1 of the front half is completed by the moving inspection device body 30.

Then, when the inspection in the divided region A1 of the front half is completed, the moving inspection device body 30 is turned 180° (pivotal turn) by rotating the right and left wheels 32 forward and backward, so that the flaw detection heads 44 are directed to a side edge A2a (opposite side to the side edge A1a) of the divided region A2 facing the above-described center line (straight line). Even when the divided region A2 of the rear half is inspected while the flaw detection heads 44 are directed to the side edge A1a side of the divided region A1 without turning the moving inspection device body 30 180°, a region between the flaw detection heads 44 and the side edge A2a of the divided region A2 becomes a range where the inspection cannot be performed because the flaw detection heads 44 cannot be moved by the scanning actuator.

Then, an inspection path and a movement path similar to those in the front half are repeated in the state where the flaw detection heads 44 are directed to the side edge A2a side of the divided region A2 facing the center line (straight line), so that the inspection in the divided region A2 of the rear half is completed by the moving inspection device body 30. This makes it possible to inspect the entire rectangular inspection region of the surface Sa of the rectangular steel plate S as the inspection target.

Therefore, the present invention has been made based on this finding. In order to solve the above-described problems, a moving inspection device according to one aspect of the present invention includes a moving inspection device body configured to inspect an inspection target for defects while moving over the surface of the inspection target, in which the moving inspection device body includes: a carriage configured to move by at least two wheels capable of rotating forward and backward over the surface of the inspection target in the forward and backward direction orthogonal to rotation shafts of the wheels; and at least one inspection sensor arranged on the front end side or the rear end side of the carriage and configured to inspect the inspection target for defects, an inspection region of the inspection target is divided into two divided regions across a straight line, and the carriage of the moving inspection device body is configured to move in a state where the inspection sensor is directed to the side edge side of the divided region facing the straight line in each of the two divided regions.

A moving inspection method according to another aspect of the present invention includes inspecting an inspection target for defects using the above-described moving inspection device.

A method for manufacturing a steel material according to another aspect of the present invention includes an inspection step of implementing the above-described moving inspection method.

Advantageous Effects of Invention

The moving inspection device, the moving inspection method, and the method for manufacturing a steel material according to the present invention can provide a moving inspection device capable of appropriately inspecting an inspection target while realizing the simplification of the configuration and significant size reduction/weight reduction of the device, a moving inspection method, and a method for manufacturing a steel material.

DESCRIPTION OF EMBODIMENTS

Hereinafter, embodiments of the present invention will now be described with reference to the drawings. The following embodiments illustrate devices and methods for embodying the technical idea of the present invention. The technical idea of the present invention does not specify materials, shapes, structures, arrangement, and the like of constituent parts to the following embodiments. The drawings are schematic. Therefore, it should be noted that the relationship, ratio, and the like between the thickness and the planar dimension are different from the actual relationship, ratio, and the like. The drawings include portions different in mutual dimensional relationships and ratios.

First, the entire inspection system including a moving inspection device according to one embodiment of the present invention is described with reference to FIG. 1.

Figure 1:
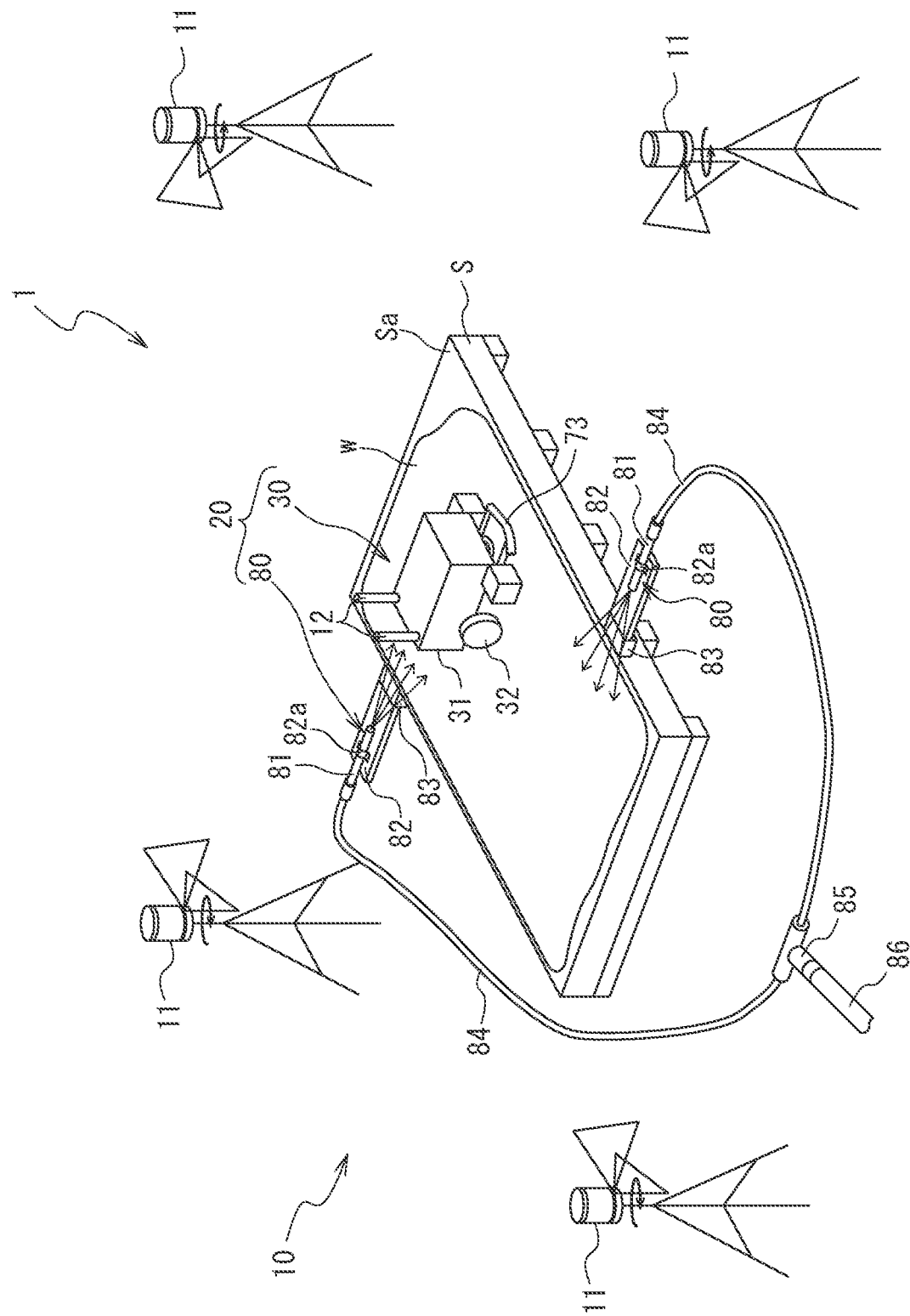
FIG. 1 is a view illustrating the schematic configuration of the entire inspection system including a moving inspection device according to one embodiment of the present invention.

FIG. 1 illustrates the schematic configuration of the entire inspection system including the moving inspection device according to one embodiment of the present invention. An inspection system 1 includes an indoor position measuring system 10 and a moving inspection device 20.

The indoor position measuring system 10 measures the self-position indoors based on the principle of triangulation and uses an indoor global positioning system (IGPS) in this embodiment. Specifically, the indoor position measuring system 10 includes a plurality of navigation transmitters 11 arranged indoors, navigation receivers 12, and a current position calculation unit 13 (see FIG. 2) calculating the position of a moving inspection device body 30 by position calculation software.

The moving inspection device 20 includes the moving inspection device body 30 inspecting a steel plate S as an inspection target for internal defects of the steel plate S and surface defects of the rear surface side of the steel plate S while moving over the surface Sa of the steel plate S and water supply devices 80 suppling water W required for the inspection onto the surface Sa of the steel plate S. As the steel plate S as the inspection target, a thick steel plate (plate thickness of 6 mm or more) having a rectangular shape as viewed from the plane is targeted herein.

Figure 3:
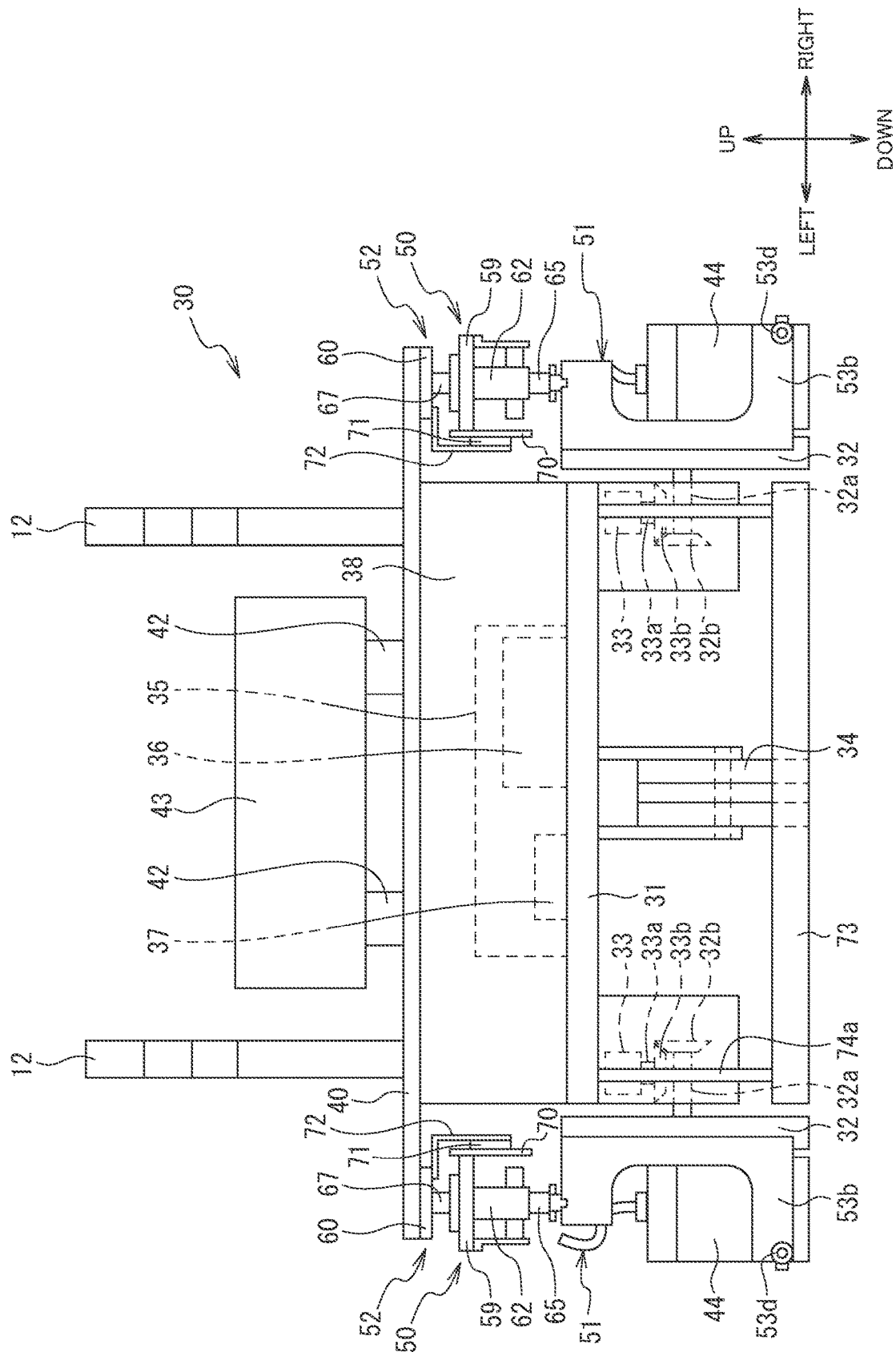
FIG. 3 is a front view of a moving inspection device body constituting the moving inspection device according to one embodiment of the present invention.
Figure 4:
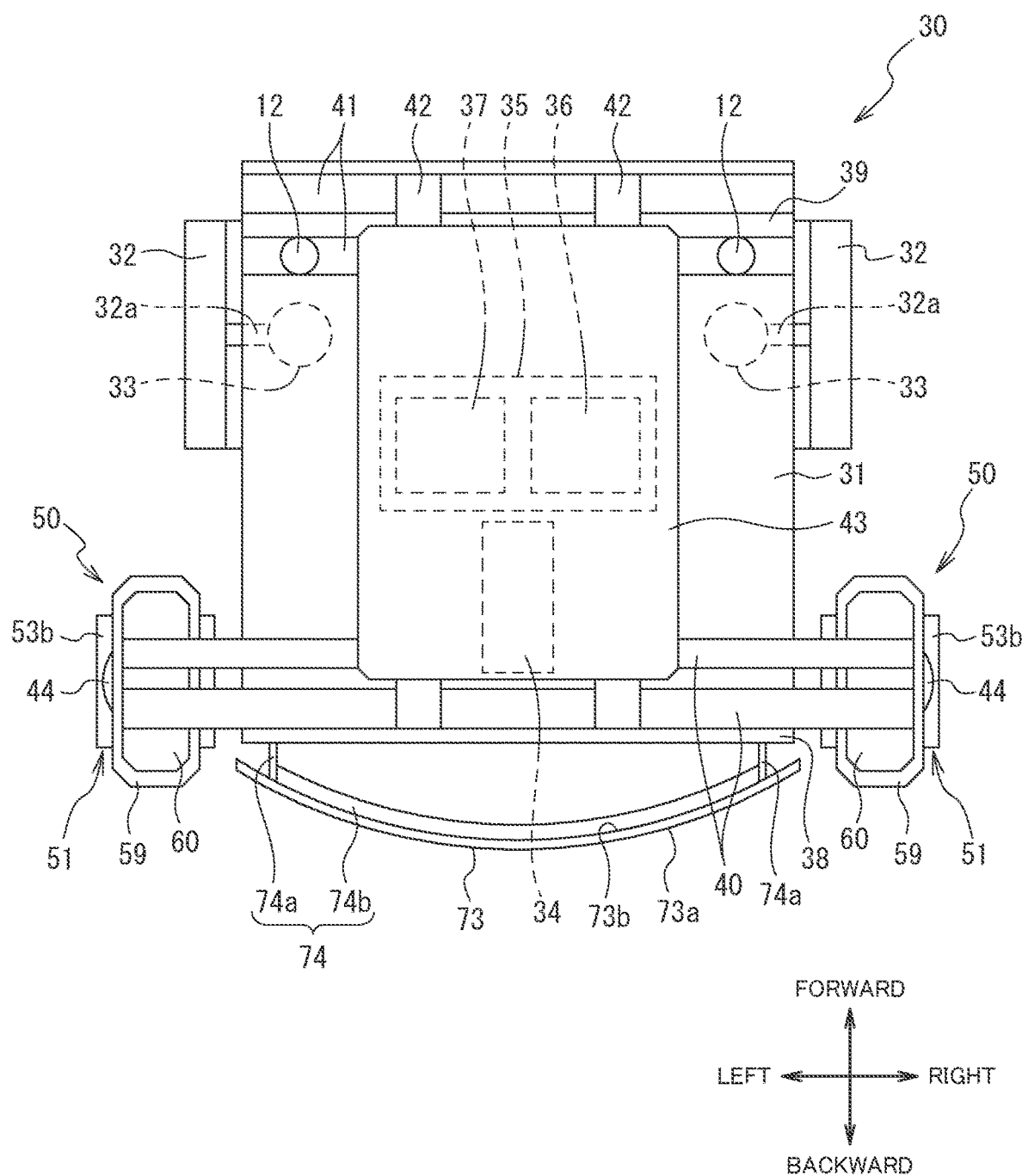
FIG. 4 is a plan view of the moving inspection device body illustrated in FIG. 3.
Figure 5:
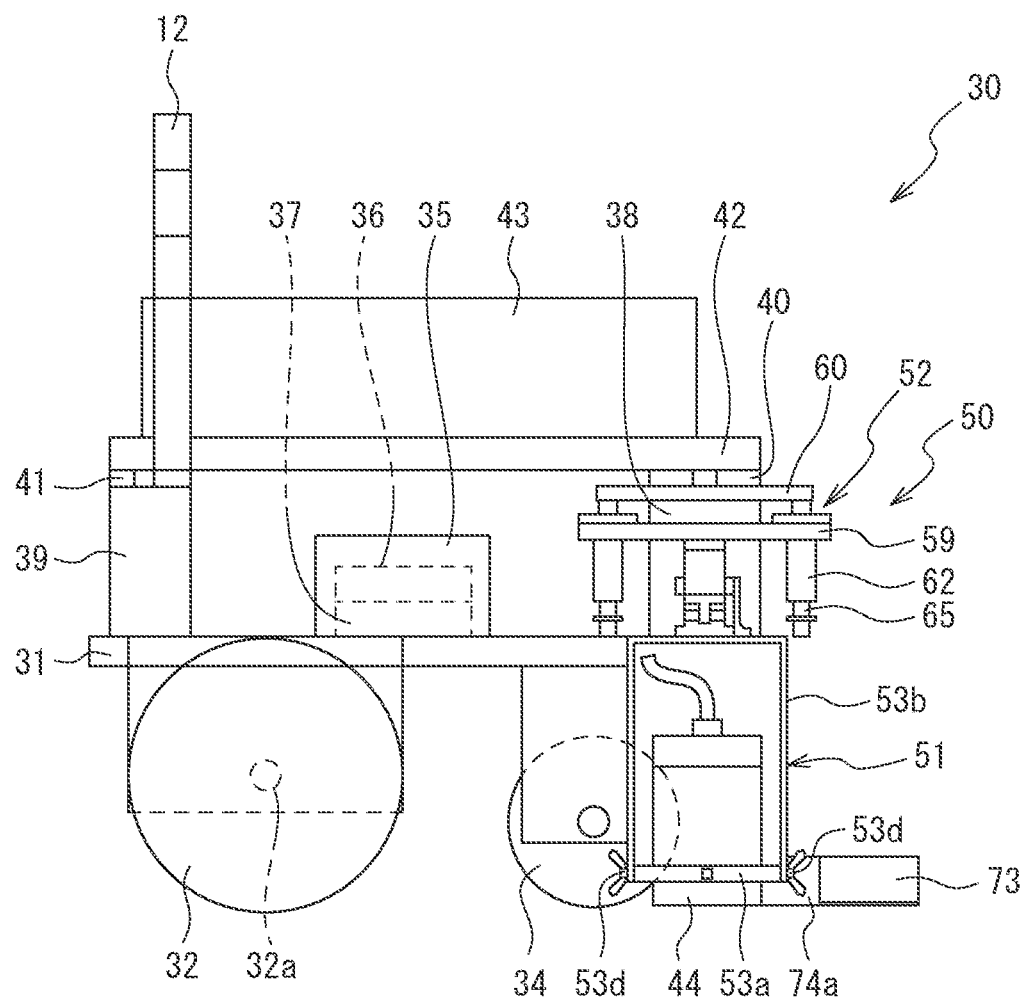
FIG. 5 is a left side view of the moving inspection device body illustrated in FIG. 3.
Figure 5:
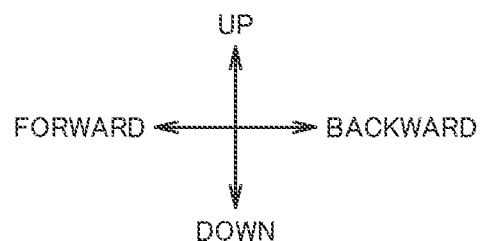
Figure 6:
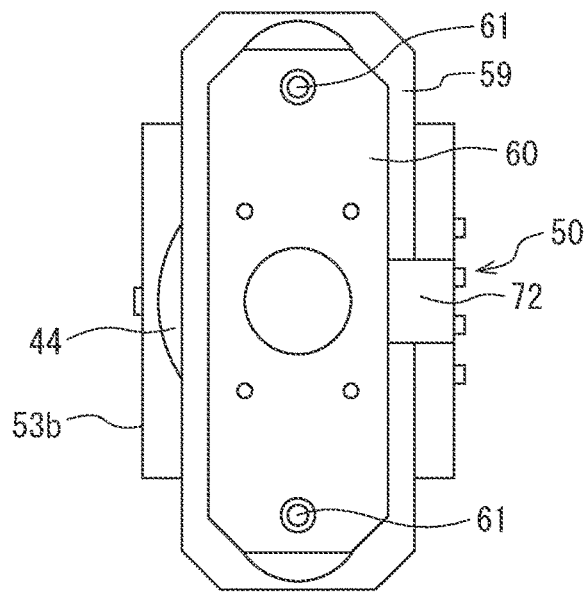
FIG. 6 is a plan view of a follow-up mechanism causing a mounted head to follow the uneven state of the surface of the steel plate in the moving inspection device body illustrated in FIG. 3.

The moving inspection device body (hereinafter referred to as "inspection device body") 30 has a carriage 31 having a predetermined plate thickness and having a substantially rectangular shape extending in the right and left direction and in the forward and backward direction as illustrated in FIG. 3 to FIG. 5. The carriage 31 is provided with a pair of right and left wheels 32 on both sides in the right and left direction on the front side. The pair of right and left wheels 32 is individually and independently driven. Each wheel 32 has a rotation shaft 32a having first intersecting axis gears 32b at the tip as illustrated in FIG. 3. The first intersecting axis gears 32b are meshed with second intersecting axis gears 33b provided at the tip of an output rotation shaft 33a of a speed reduction gear of a wheel driving motor 33. Each wheel 32 can be rotated forward and backward by the wheel driving motor 33. The carriage 31 is further installed with a driven wheel 34 capable of moving in all directions in a substantially center part in the right and left direction on the rear side of the undersurface side.

The carriage 31 moves in the forward and backward direction orthogonal to the rotation shaft 32a of each wheel 32 over the surface Sa of the steel plate S by the pair of right and left wheels 32 capable of rotating forward and backward.

The carriage 31 is further provided with flaw detection heads 44 each including with an ultrasonic probe as inspection sensors detecting internal defects of the steel plate S and surface defects of the rear surface side of the steel plate S and an ultrasonic flaw detector body 43 into which outputs (results) from the flaw detection heads 44 are input and which data (calculation)—processes the outputs (results) and outputs the data processing results to an IO board 37 described below.

As illustrated in FIG. 3 to FIG. 5, a first raised part 38 extending in the right and left direction is erected near the rear end of the upper surface of the carriage 31 and a second raised part 39 extending in the right and left direction is erected near the front end of the upper surface of the carriage 31. As illustrated in FIG. 3 to FIG. 5, a plurality of first plate members 40 extending in the right and left direction to project from the ends in the right and left direction of the carriage 31 is installed on the upper surface of the first raised part 38 and a plurality of second plate members 41 extending in the right and left direction is installed on the upper surface of the second raised part 39. Further, a plurality of third plate members 42 extending in the forward and backward direction is installed to bridge the first plate members 40 and the second plate members 41 on the upper surfaces the first plate members 40 and the upper surfaces of the second plate members 41. On the upper surfaces of the third plate members 42, the above-described ultrasonic flaw detector body 43 is installed.

A pair of right and left flaw detection heads 44 is installed on the rear end sides of the carriage 31 below the first plate members 40 projecting from the ends in the right and left direction end of the carriage 31 as illustrated in FIG. 3 to FIG. 5. Each flaw detection head 44 is supported to the first plate members 40 by a follow-up mechanism 50 causing the flaw detection head 44 to follow the unevenness state of the surface Sa of the steel plate S as the inspection target. The follow-up mechanism 50 is described in detail later.

The installation distance between the pair of right and left flaw detection heads 44 is set to a size of an integral multiple of an inspection pitch D described later.

Further, a pair of navigation receivers 12 is erected near both the right and left ends on the second plate member 41 and an on-board computer 36 and an IO board 37 are provided in a control box 35 on the upper surface of the carriage 31.

Each navigation transmitter 11 of the indoor position measuring system 10 emits rotating fan beams. Each navigation receiver 12 receives the rotating fan beams emitted from each navigation transmitter 11. At this time, the rotating fan beams are deviated at a predetermined angle, and the three-dimensional coordinate values, i.e., the position or the height, of the navigation receivers 12 receiving the rotating fan beams can be measured. Reception information received by the navigation receivers 12 is transmitted to the on-board computer 36, and the positions of the navigation receivers 12 are calculated by the on-board computer 36 according to the principle of triangulation. By the use of signals received from the plurality of navigation transmitters 11 and by repeating the calculation, position information of the traveling inspection device body 30 mounted with the navigation receivers 12 can be acquired in real time.

The On-board computer 36 is a computer system constituted to include a ROM, a RAM, a CPU, and the like and realizing each function described later on software by executing various dedicated programs stored in advance in the ROM and the like.

Figure 2:
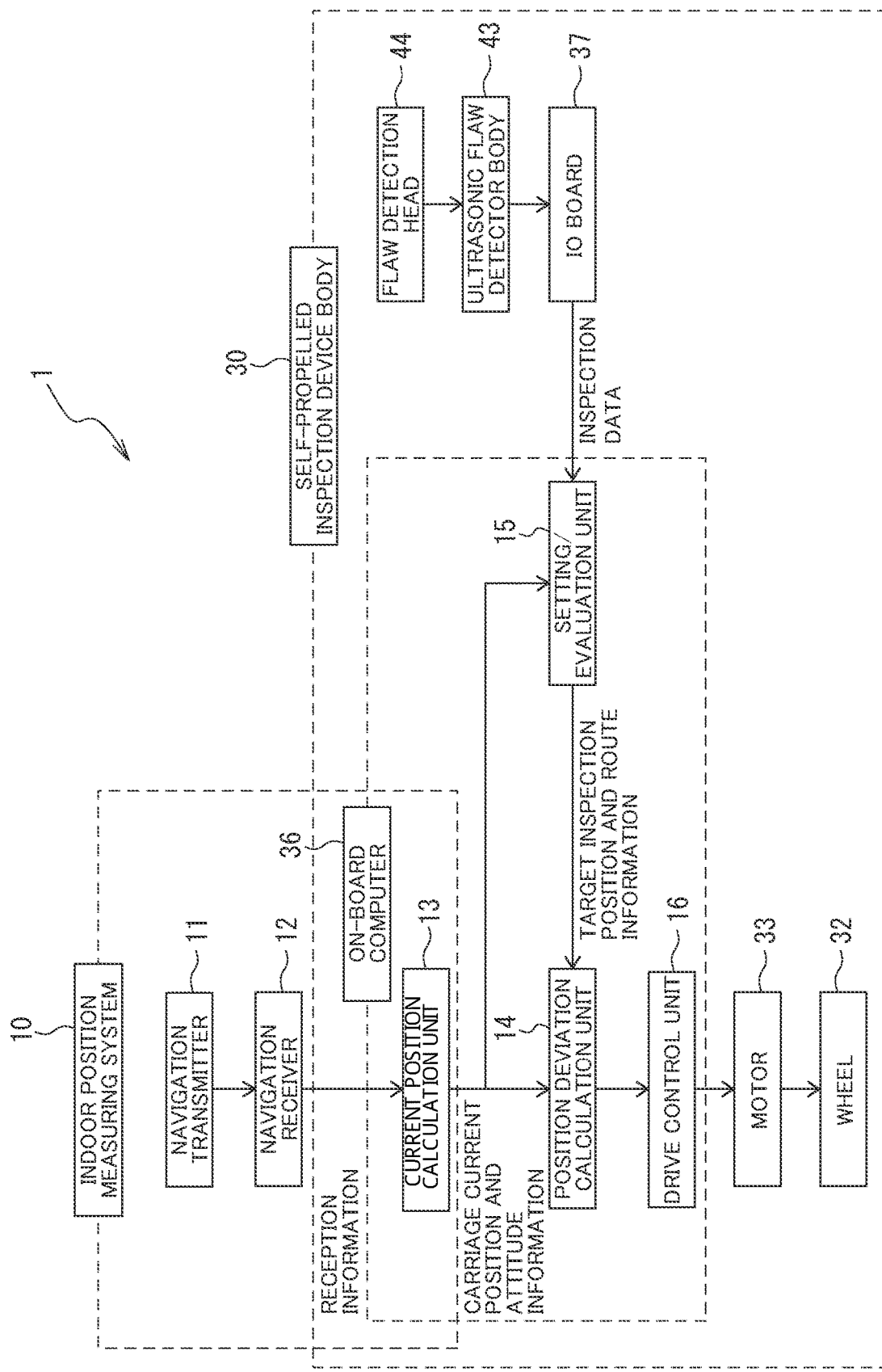
FIG. 2 is a block diagram of the inspection system illustrated in FIG. 1.

As illustrated in FIG. 2, the on-board computer 36 includes the current position calculation unit 13 calculating the current position of each navigation receiver 12 based on the reception information received by each navigation receiver 12. The on-board computer 36 further includes a setting/evaluation unit 15 setting a target inspection position and route information and evaluating inspection data and inspection position information from the IO board 37. The on-board computer 36 further includes a position deviation calculation unit 14 calculating a deviation of the current position with respect to the target inspection position based on the current position of each navigation receiver 12 calculated by the current position calculation unit 13 and the target inspection position from the setting/evaluation unit 15. The on-board computer 36 further includes a drive control unit 16 outputting a control signal, such as a speed command, to the wheel driving motor 33 such that the deviation calculated by the position deviation calculation unit 14 is 0 and performing feedback control of the speed (including the rotation direction) of the wheels 32. The drive control unit 16 outputs a control signal, such as a speed command, to the wheel driving motor 33 such that the deviation is 0 and performs the feedback control of the speed (including the rotation direction) of the wheels 32, so that the inspection device body 30 autonomously travels along the target travel route.

Although not illustrated, the carriage 31 is mounted with a battery as a power source.

Next, the follow-up mechanism 50 causing each flaw detection head 44 to follow the uneven state of the surface Sa of the steel plate S is described with reference to FIG. 6 to FIG. 10.

Figure 10:
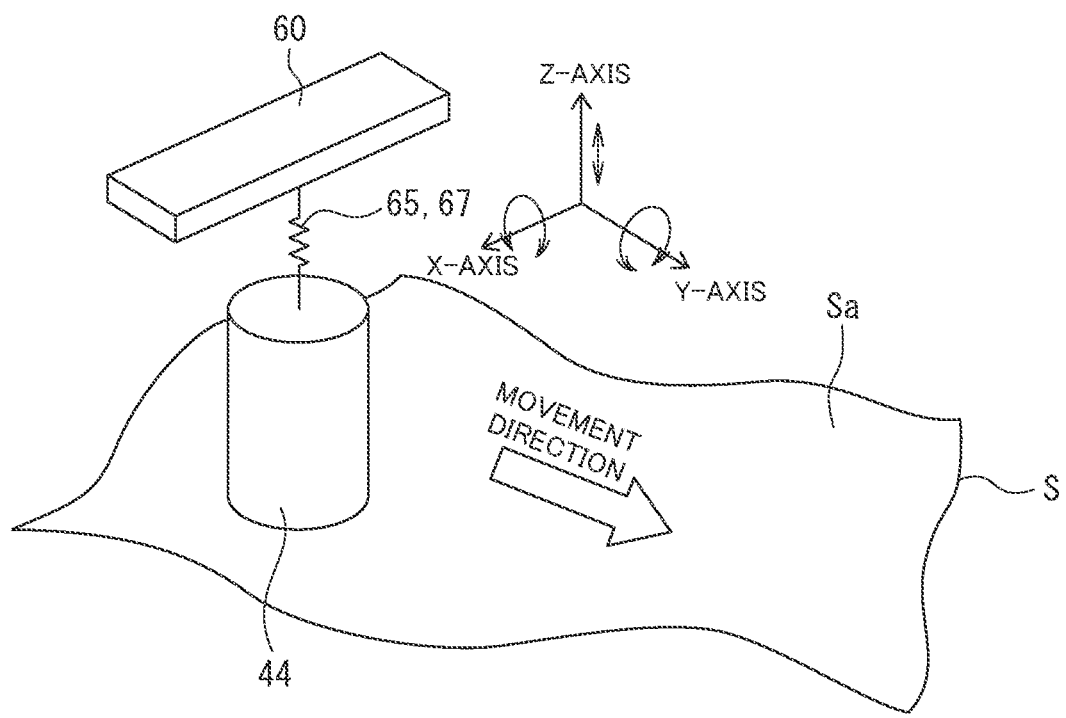
FIG. 10 is a schematic diagram for explaining the follow-up mechanism in the moving inspection device body illustrated in FIG. 3.

Herein, as illustrated in FIG. 10, the uneven state of the surface Sa of the steel plate S means not only a case where the surface Sa of the steel plate S has unevenness but all cases where the surface Sa of the steel plate S is uneven, also including a case where the surface Sa of the steel plate S has waviness.

The follow-up mechanism 50 includes a sensor holding mechanism 51 holding the flaw detection head 44 as the inspection sensor and a load adjustment mechanism 52 adjusting a load applied to the surface Sa of the steel plate S by the flaw detection head 44 held by the sensor holding mechanism 51.

Figure 8:
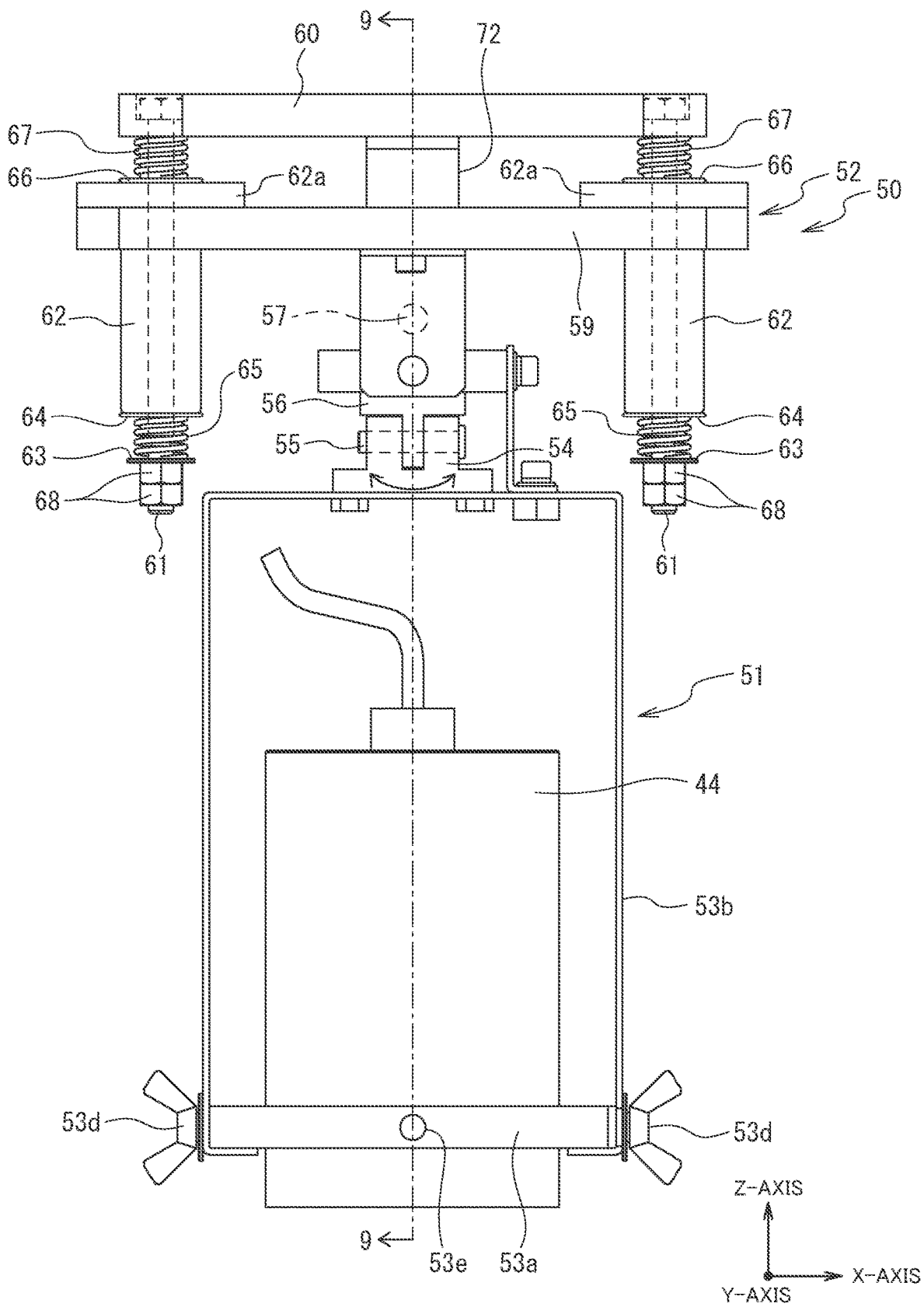
FIG. 8 is a left side view of the follow-up mechanism causing the mounted head to follow the uneven state of the surface of the steel plate in the moving inspection device body illustrated in FIG. 3.
Figure 9:
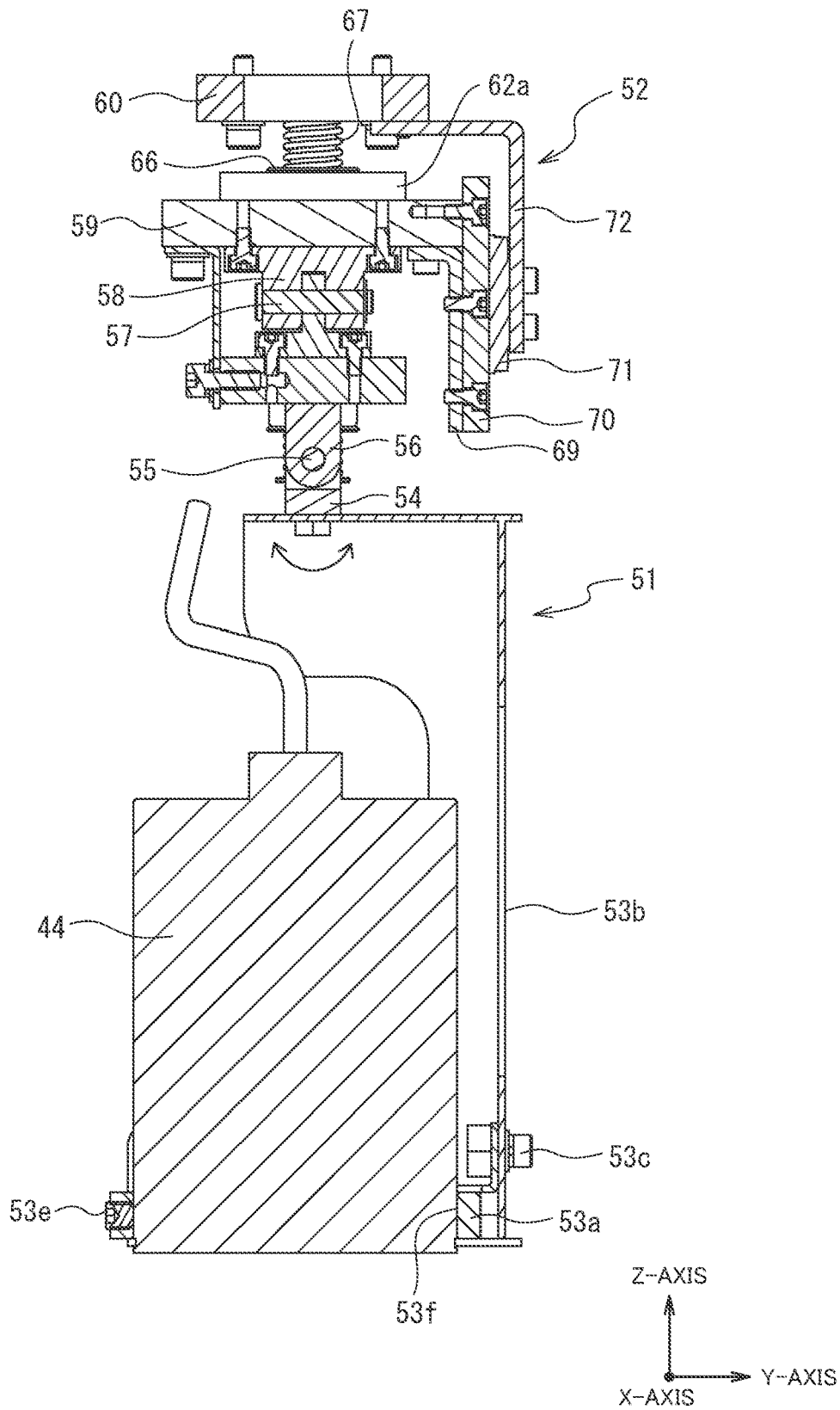
FIG. 9 is a cross-sectional view cut along the line 9-9 in FIG. 8.

The sensor holding mechanism 51 includes a flat plate-like holder 53a holding the flaw detection head 44 to surround the periphery of the flaw detection head 44 as illustrated in FIG. 8. As illustrated in FIG. 9, the flaw detection head 44 is inserted into a through hole 53f formed in the center of the holder 53a, and the flaw detection head 44 is pressed from the outer periphery by a screw member 53e to be held by the holder 53a. The sensor holding mechanism 51 further includes a sensor holding frame member 53b fixing the holder 53a holding the flaw detection head 44 and surrounding the flaw detection head 44 from the periphery. The holder 53a is fixed to the sensor holding frame member 53b by a bolt 53c and a wing bolt 53d.

As illustrated in FIG. 8 and FIG. 9, a first support member 54 is fixed to the upper surface of the sensor holding frame member 53b and the first support member 54 is rotatably supported around a first hinge 55 with respect to a second support member 56. The first hinge 55 extends in the X-axis direction as illustrated in FIG. 8 and FIG. 9. More specifically, the sensor holding frame member 53b holding the flaw detection head 44 is configured to rotate around the X-axis. The X-axis extends in parallel to and in the forward and backward (width) direction with respect to the surface Sa of the steel plate S.

As illustrated in FIG. 9, the second support member 56 is rotatably supported around a second hinge 57 with respect to a third support member 58. The second hinge 57 extends in the Y-axis direction as illustrated in FIG. 8 and FIG. 9. More specifically, the sensor holding frame member 53b holding the flaw detection head 44 is configured to rotate around the Y-axis. The Y-axis extends in the right and left (longitudinal) direction parallel to the surface Sa of the steel plate S and orthogonal to the X-axis.

Figure 7:
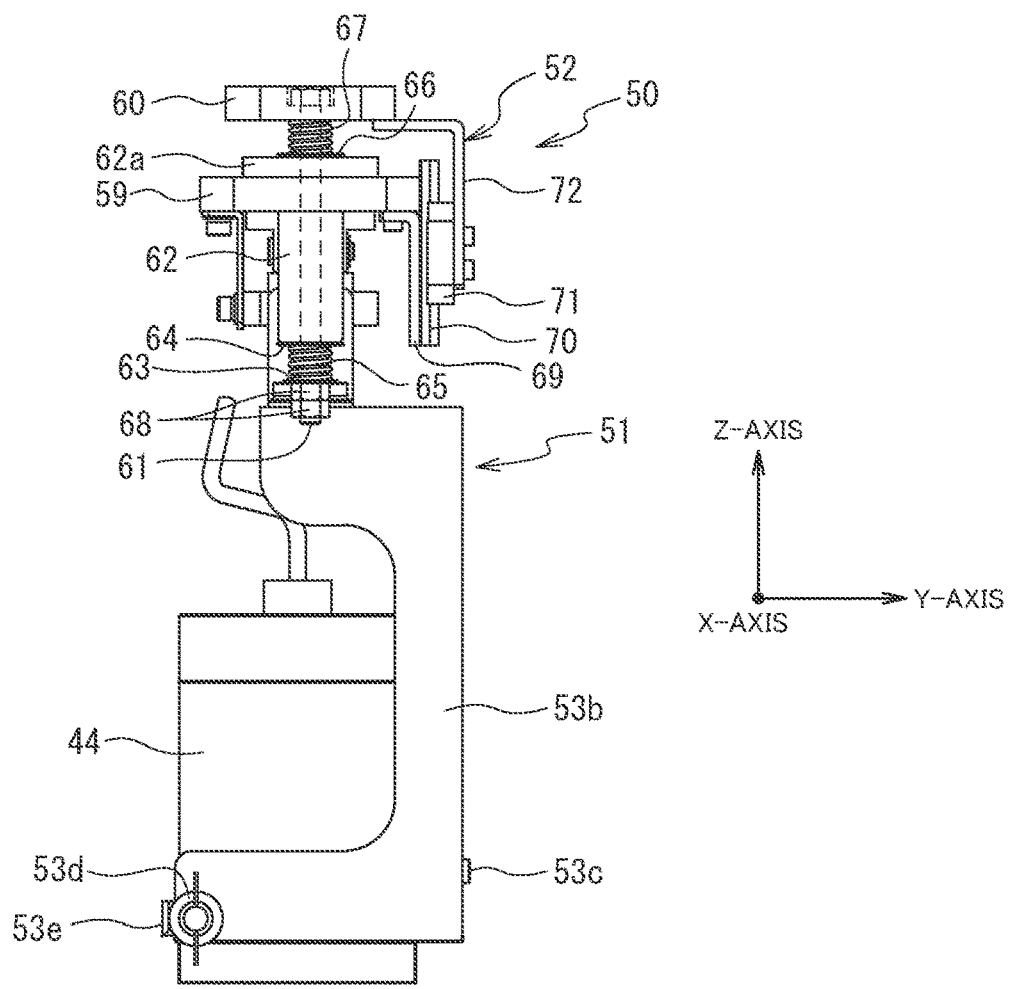
FIG. 7 is a front view of the follow-up mechanism causing the mounted head to follow the uneven state of the surface of the steel plate in the moving inspection device body illustrated in FIG. 3.

Each of the rotation around the X-axis and the rotation around the Y-axis of the sensor holding frame member 53b is regulated in some cases. Considering the cases, FIG. 7 to FIG. 9 illustrate members regulating each of the rotation around the X-axis and the rotation around the Y-axis of the sensor holding frame member 53b.

As illustrated in FIG. 9, the third support member 58 is attached to the undersurface of a lower flat plate 59 having a predetermined plate thickness and extending in the right and left direction and in the forward and backward direction. An end part in the right and left direction of the lower flat plate 59 is attached with an attachment plate 69 and a rail member 70 extending in the Z-axis direction. Above the lower flat plates 59, upper flat plates 60 having a predetermined plate thickness and extending in the right and left direction and in the forward and backward direction are provided. As illustrated in FIG. 3, the upper flat plates 60 are attached to the undersurfaces of the first plate members 40 projecting from the ends in the right and left direction of the carriage 31. To the undersurfaces of the upper flat plates 60, attachment plate parts 72 each attached with a slider 71 at the tip are fixed. The slider 71 is configured to move along the rail member 70 attached to the lower flat plate 59. More specifically, the slider 71 is fixed to the upper flat plate 60 fixed to the first plate member 40 fixed to the carriage 31, and therefore the lower flat plate 59 moves up and down along a direction in which the rail member 70 extends. Therefore, the sensor holding frame member 53b holding the flaw detection head 44 is configured to move up and down along the Z-axis extending perpendicularly (up and down) to the surface Sa of the steel plate S.

Next, the load adjustment mechanism 52 adjusts a load applied to the surface Sa of the steel plate S by the flaw detection head 44 held by the sensor holding mechanism 51. As described above, the sensor holding frame member 53b holding the flaw detection head 44 moves up and down along the Z-axis extending perpendicularly (up and down) to the surface Sa of the steel plate S. Therefore, when no load acts on the sensor holding frame member 53b, the self-weight of the entire configuration up to the lower flat plate 59 including the flaw detection head 44 and the sensor holding frame member 53b acts on the surface Sa of the steel plate S. When the self-weight of the entire configuration up to the lower flat plate 59 including the flaw detection head 44 and the sensor holding frame member 53b acts on the surface Sa of the steel plate S, the load is excessively large in the flaw detection by the flaw detection head 44, which hinders the flaw detection. Therefore, in this embodiment, the load adjustment mechanism 52 adjusts the load applied to the surface Sa of the steel plate S by the flaw detection head 44.

In the load adjustment mechanism 52, bushes 62 each including a flange 62a at one end of a hollow pipe part are press-fitted and fixed to the vicinity of both ends in the forward and backward direction of the lower flat plate 59 such that the flange 62a is in contact with the upper surface of the lower flat plate 59 and the hollow pipe part is inserted through the lower flat plate 59 and projects downward from the lower flat plate 59 as illustrated in FIG. 8. A shaft 61 inserted through each bush 62 is fixed to the upper flat plate 60. Near the lower end of each shaft 61, a male screw part is formed and a plurality of nuts 68 for load adjustment is screwed into the male screw part. A metal washer 63 is arranged above each nut 68, a metal washer 64 is arranged below each bush 62, and a compression coil spring 65 is arranged to surround each shaft 61 between both the metal washers 63, 64. The compression coil spring 65 acts to push the lower flat plate 59, i.e., the entire configuration up to the lower flat plate 59 including the flaw detection head 44 and the sensor holding frame member 53b, upward via the bush 62. On the other hand, a metal washer 66 is arranged above the flange 62a of the bush 62 and a compression coil spring 67 is arranged to surround the shaft 61 between the metal washer 66 and the undersurface of upper flat plate 60. The compression coil spring 67 acts to push the lower flat plate 59, i.e., the entire configuration up to the lower flat plate 59 including the flaw detection head 44 and the sensor holding frame member 53b, downward via the bush 62. By adjusting the push-up force by the compression coil spring 65 and the push-down force by the compression coil spring 67, the load applied to the surface Sa of the steel plate S by the entire configuration up to the lower flat plate 59 including the flaw detection head 44 and the sensor holding frame member 53b is adjusted.

In usual, the load is adjusted such that a value obtained by subtracting the push-down force by the compression coil spring 67 from the push-up force by the compression coil spring 65 is positive. Thus, it is configured so that the entire configuration up to the lower flat plate 59 including the flaw detection head 44 and the sensor holding frame member 53b is pushed upward, so that the self-weight of the entire configuration up to the lower flat plate 59 including the flaw detection head 44 and the sensor holding frame member 53b acting on the surface Sa of the steel plate S is subtracted.

Thus, the load applied to the surface Sa of the steel plate S by the flaw detection head 44 is adjusted.

As described above, the follow-up mechanism 50 includes the sensor holding mechanism 51 holding the flaw detection head 44 as the inspection sensor and the load adjustment mechanism 52 adjusting the load applied to the surface Sa of the steel plate S by the flaw detection head 44 held by the sensor holding mechanism 51. The sensor holding mechanism 51 rotates around the X-axis extending in parallel to the surface Sa of the steel plate S and the Y-axis extending in a direction parallel to the surface Sa of the steel plate S and orthogonal to the X-axis, and moves up and down along the Z-axis extending perpendicularly to the surface Sa of the steel plate S.

Thus, as illustrated in FIG. 10, when the flaw detection head 44 scans (moves over) the surface Sa of the steel plate S, the flaw detection head 44 held by the sensor holding mechanism 51 rotates around the X-axis and the Y-axis in a state where a predetermined load is applied to the surface Sa of the steel plate S according to the uneven state of the surface Sa of the steel plate S. Further, the flaw detection head 44 can move up and down along the Z-axis, and thus the flaw detection head 44 can follow the uneven state of the surface Sa of the steel plate S with an appropriate pressing force.

As illustrated in FIG. 3 to FIG. 5, the inspection device body 30 is installed with a flow adjustment plate 73.

The flow adjustment plate 73 is installed with a flow adjustment plate attachment member 74 on the undersurface of the carriage 31 to project from the carriage 31 in the advancing direction (backward direction) in an inspection path of the inspection device body 30 as illustrated in FIG. 3 to FIG. 5.

The inspection device body 30 advances toward the backward side of the carriage 31 in the inspection path and advances to the front side of the carriage 31 in a movement path, which is described later.

The flow adjustment plate attachment member 74 includes a pair of right and left support leg parts 74a extending downward from the undersurface of the carriage 31 and an arc-shaped attachment plate part 74b attached to the rear ends of both the support leg parts 74a to be bridged therebetween and having a projecting and arc-shaped rear side.

As illustrated in FIG. 4, the flow adjustment plate 73 has a first arc surface 73a and a second arc surface 73b having a slightly smaller diameter than the diameter of the first arc surface 73a, has an arc shape formed into a predetermined plate thickness, and is attached to the rear surface of the arc-shaped attachment plate part 74b such that the first arc surface 73a projects toward the advancing direction in the inspection path of the inspection device body 30. The flow adjustment plate 73 is attached to the arc-shaped attachment plate part 74b to form a gap such that a water film is formed between the flow adjustment plate 73 and the surface Sa of the steel plate S.

The flow adjustment plate 73 pushes out the water W supplied onto the surface Sa of the steel plate S from the water supply devices 80 in the advancing direction and forms streamlines for supplying the water between the flaw detection heads 44 and the surface Sa of the steel plate S simultaneously with the movement of the inspection device body 30.

Next, the water supply devices 80 are described. The inspection device body 30 inspects the steel plate S for internal defects of the steel plate S and surface defects of the rear surface side of the steel plate S by ultrasonic the flaw detection, and therefore the surface (inspection surface) Sa of the steel plate S requires water as a medium for passing ultrasonic waves. To spray this water onto the surface Sa of the steel plate S, the moving inspection device 20 includes the water supply devices 80 supplying the water W required for the inspection onto the surface Sa of the steel plate S as illustrated in FIG. 1.

The water supply devices 80 are provided separately from the inspection device body 30. In this embodiment, as illustrated in FIG. 1, a pair of water supply devices 80 is installed on the end surfaces on the long-side sides facing each other of the steel plate S formed in a rectangular shape.

Each water supply device 80 includes a nozzle 81 supplying the water W onto the surface Sa of the steel plate S as illustrated in FIG. 1. The nozzle 81 includes a flat spray nozzle, and the water W is jetted from the nozzle 81 to spread in a fan shape.

Herein, the nozzle 81 is attached by a fixing member 82a onto an attachment plate 82 of a rectangular flat plate shape fixed to a magnet-type attachment base 83 such that the upper surface is flush with the attachment base 83, the attachment base 83 being detachably attached to the end surface of the steel plate S such that the upper surface is flush with the surface Sa of the steel plate S.

A hose 84 is connected to each nozzle 81, and the two hoses 84 are connected to a hose 86 connected to a water supply source (not illustrated) by a joint 85.

When the water W is supplied from the water supply source to the nozzles 81 via the hose 86 and the hoses 84, the water W is jetted from the nozzles 81 in a fan shape and supplied onto the surface Sa of the steel plate S through the upper surface of the attachment plate 82 and the upper surface of the attachment base 83. Thus, the water W is sprayed onto the surface Sa of the steel plate S.

As described above, in the moving inspection device 20 according to this embodiment, the water supply devices 80 supplying the water W required for the inspection onto the surface Sa of the steel plate S as the inspection target are installed separately from the inspection device body 30, and therefore the inspection device body 30 itself is reduced in size and weight, so that the moving inspection device 20 capable of realizing significant size reduction/weight reduction can be achieved. One in which a water tank is installed in the inspection device body 30 itself requires, when the water W is used up, labor of supplying the water W to the water tank again. However, the moving inspection device 20 according to this embodiment has eliminated a fear of using up water.

Figure 11:
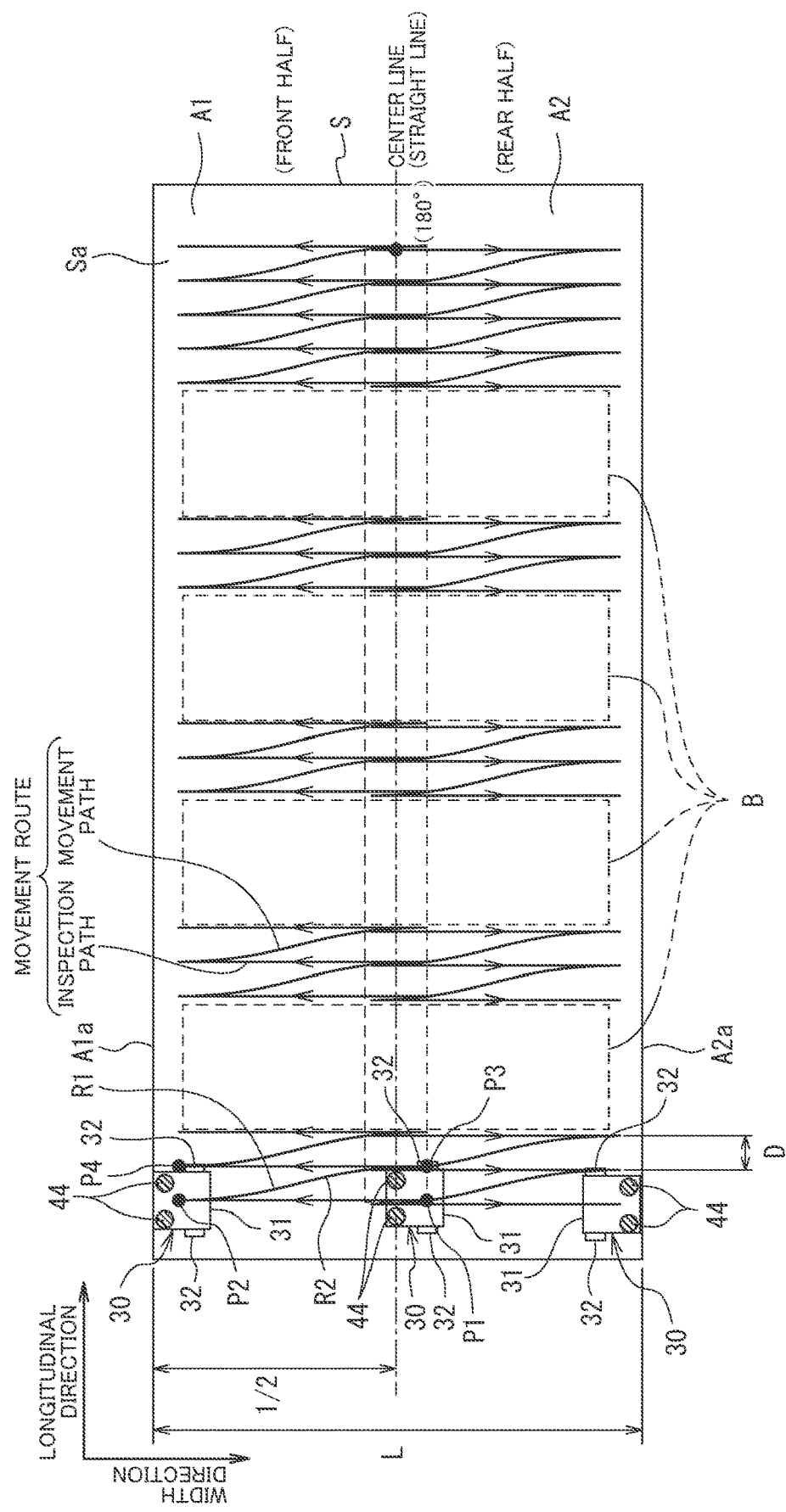
FIG. 11 is a view for explaining a movement route of the moving inspection device body when detecting flaws inside a steel plate as an inspection target.
Figure 12:
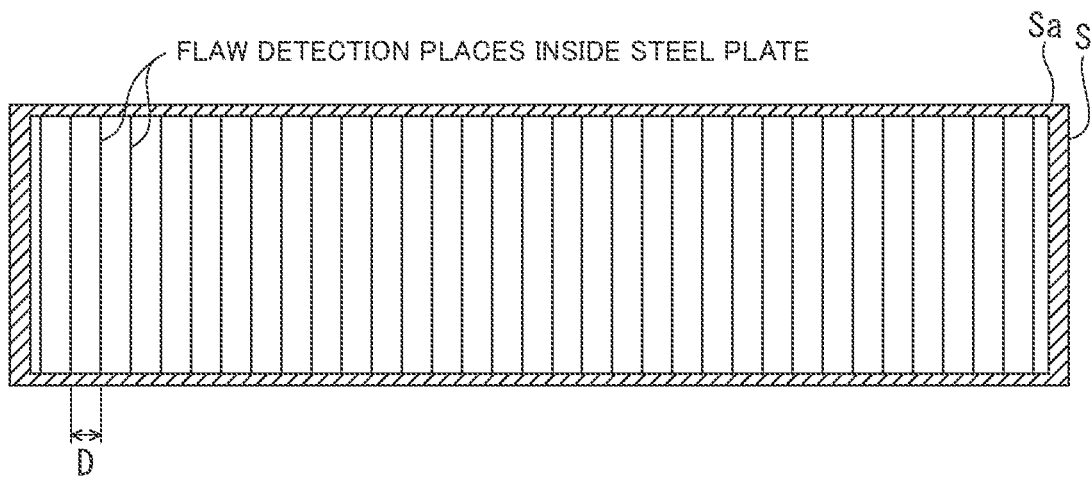
FIG. 12 is a view illustrating an example of an inspection pattern according to JIS G0801: Ultrasonic testing of steel plates for pressure vessels, in which the moving inspection device body moves in the movement route illustrated in FIG. 11 to detect flaws inside the steel plate.
Figure 16:
FIG. 16 is a view illustrating a state where an inspection region of the steel plate as the inspection target is divided into two divided regions across the center line (straight line)
Figure 16:
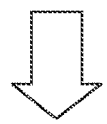
Figure 16:
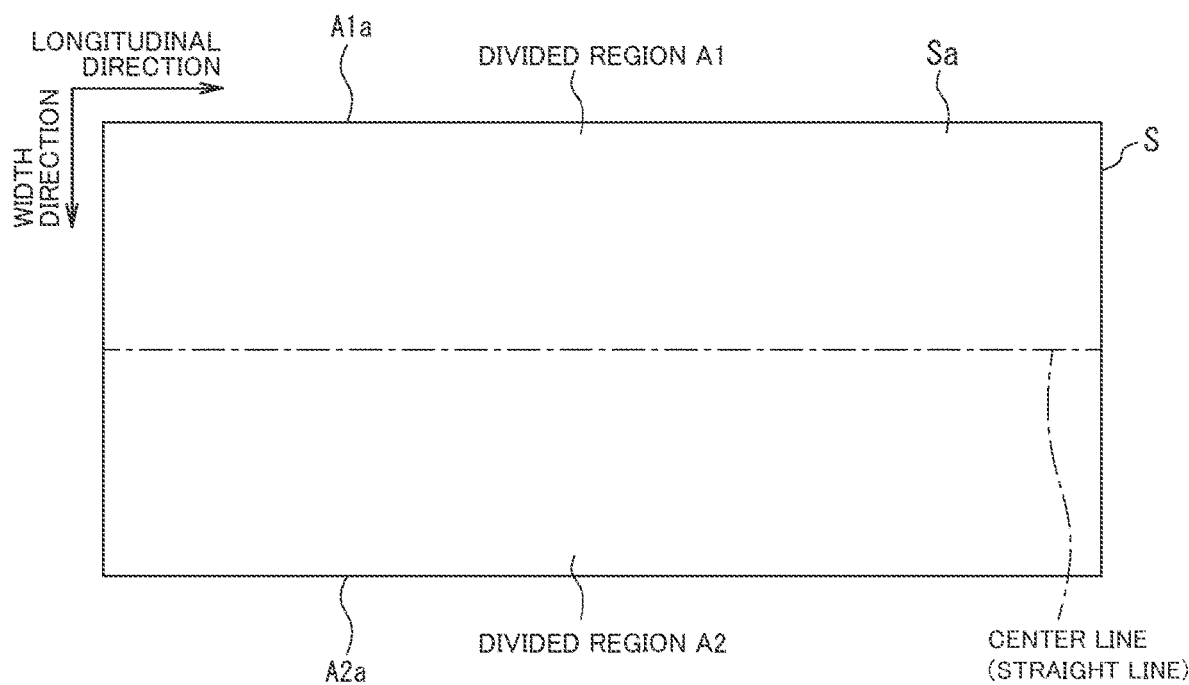
Figure 17:
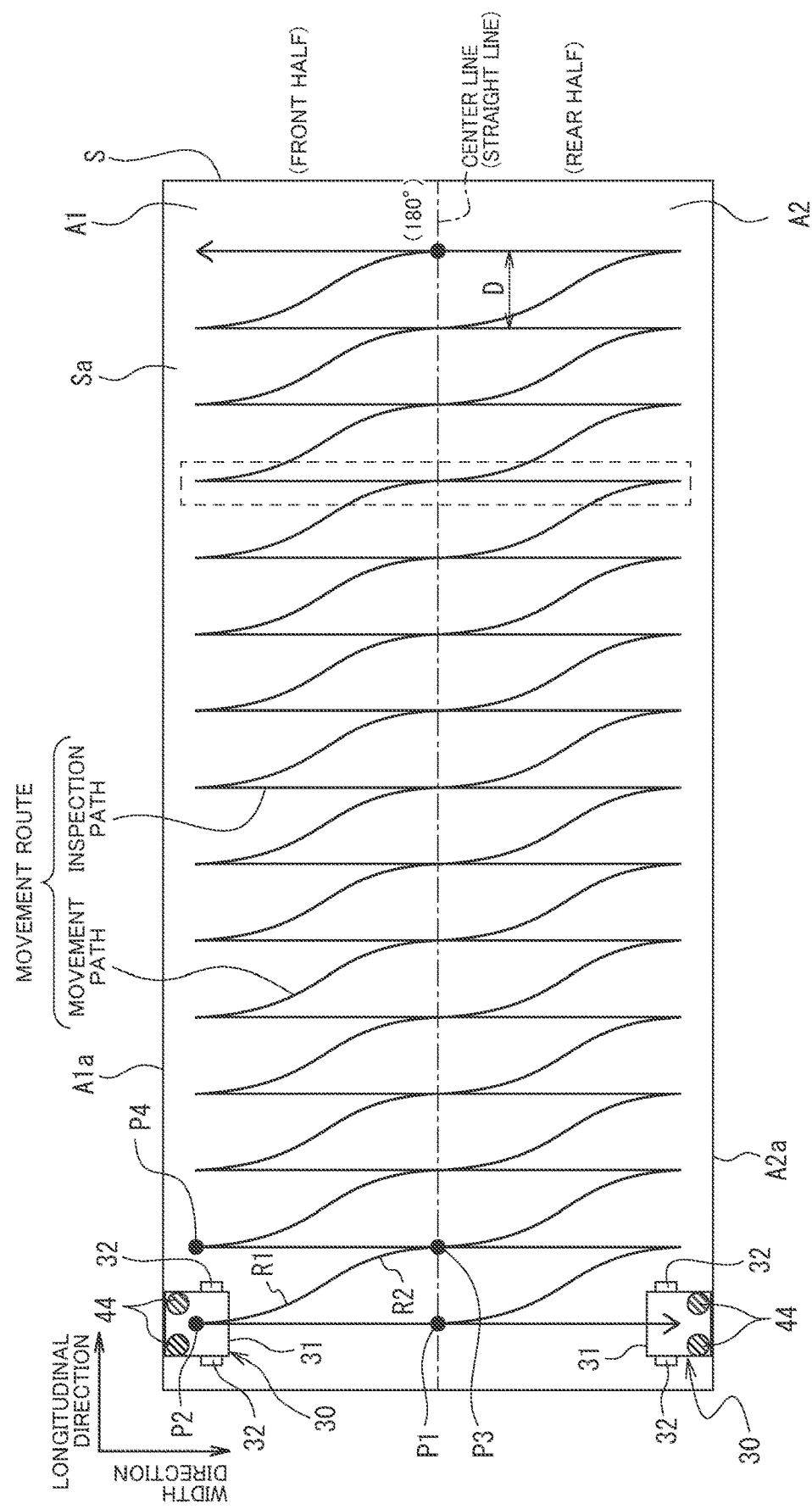
FIG. 17 is a view for explaining the movement route of the moving inspection device body of the present embodiment when inspecting the steel plate as the inspection target.

Next, a moving inspection method using the moving inspection device 20 illustrated in FIG. 1 is described with reference to FIG. 11, FIG. 12, and FIG. 16. FIG. 11 is a view for explaining a movement route of a moving inspection device body when detecting flaws inside a steel plate as the inspection target. FIG. 12 is a view illustrating an example of an inspection pattern according to JIS G0801: Ultrasonic testing of steel plates for pressure vessels, in which the moving inspection device body moves in the movement pattern illustrated in FIG. 11 to detect flaws inside the steel plate. FIG. 16 is a view illustrating the state where the inspection region of the steel plate as the inspection target is divided into two divided regions across the center line (straight line), which is described above.

First, in the moving inspection of the steel plate S using the moving inspection device 20, the water W is supplied onto the surface Sa of the steel plate S as the inspection target from the water supply devices 80, so that the water W is uniformly sprayed onto the surface Sa of the steel plate S. The supply of the water W by the water supply devices 80 is constantly performed during the inspection of the steel plate S.

Then, the inspection device body 30 of the moving inspection device 20 is moved over the surface Sa of the steel plate S in the movement pattern illustrated in FIG. 11 to detect flaws inside the steel plate S.

Herein, the current position calculation unit 13 of the on-board computer 36 mounted in the inspection device body 30 calculates the current positions of the navigation receivers 12 based on the reception information received by the navigation receivers 12. The position deviation calculation unit 14 calculates a deviation of the current position with respect to the target inspection position based on the current positions of the navigation receivers 12 calculated by the current position calculation unit 13 and the target inspection position from the setting/evaluation unit 15. The drive control unit 16 outputs a control signal, such as a speed command, to the wheel driving motor 33 such that the deviation calculated by the position deviation calculation unit 14 is 0 and performs feedback control of the speed (including the rotation direction) of the wheels 32, so that the inspection device body 30 autonomously travels along the target travel route.

Herein, in order to define the movement route, i.e., the target travel route, of the inspection device body 30, an inspection region formed in a rectangular shape of the surface Sa of the rectangular steel plate S is divided into the two divided regions of the divided region A1 and the divided region A2 having the rectangular shapes across the center line (straight line) in the width direction of the steel plate S as illustrated in FIG. 16. The center line extends in the longitudinal direction of the steel plate S at the center position (L/2) in the width direction with respect to the steel plate S having a width L.

Then, in the divided region A1 of the front half, the inspection device body 30 repeats the inspection path and the movement path constituting the movement route described later from one end side in the longitudinal direction of the steel plate S (left end side of the steel plate S in FIG. 11) to the other end side in the longitudinal direction of the steel plate S (right end side of the steel plate S in FIG. 11), thereby detecting flaws inside the steel plate S.

Herein, as illustrated in FIG. 11, the carriage 31 of the inspection device body 30 is arranged such that the flaw detection heads 44 are directed to the side edge A1a of the divided region A1 facing the above-described center line (straight line) in the divided region A1 of the front half of the two divided regions A1, A2. More specifically, the carriage 31 is arranged such that the rear end side of the carriage 31 is directed to the side edge A1a of the divided region A1. Then, the carriage 31 is moved to the position where the center as viewed from the plane of the inspection device body 30 with the flaw detection heads 44 located on the above-described center line (straight line) is located at the point P1.

Subsequently, the carriage 31 of the inspection device body 30 is moved along the width direction of the steel plate S from the position where the center as viewed from the plane of the inspection device body 30 is located at the point P1 in the first inspection path in the movement route, and, simultaneously therewith, flaws inside the steel plate S are detected by the flaw detection heads 44. Then, the inspection device body 30 is stopped at a position where the center as viewed from the plane of the inspection device body 30 with the flaw detection heads 44 located at the side edge A1a of the divided region A1 is located at the point P2. More specifically, in the first inspection path, the flaw detection heads 44 detect flaws inside of the steel plate S while linearly moving from the position on the center line (straight line) to the position on the side edge A1a of the divided region A1. This eliminates the necessity of a scanning actuator moving the flaw detection heads 44 to the side edge A1a of the divided region A1.

Thereafter, the carriage 31 of the inspection device body 30 is rotated backward while giving a right/left rotational speed difference to the pair of right and left wheels 32. Thus, the center as viewed from the plane of the inspection device body 30 moves from the point P2 to the point P3 in the track containing the two curves R1, R2, and then the carriage 31 of the inspection device body 30 stops. The point P3 is a point where the flaw detection heads 44 are located at positions on the center line (straight line) different from the above-described positions on the center line (straight line) (positions where the flaw detection heads 44 are shifted by a predetermined distance (corresponding to the inspection pitch D) in the longitudinal direction of the steel plate S with respect to the initial positions of the flaw detection heads 44). The point P3 is a starting point for the next inspection path. More specifically, the flaw detection heads 44 move in the track containing the two curves R1, R2 from the positions on the side edge A1a of the divided region A1 to the other positions on the center line (straight line). In this movement path, the flaw detection is simultaneously performed by the flaw detection heads 44, but inspection data is erased by the setting/evaluation unit 15 described later.

Thereafter, the inspection path and the movement path are similarly repeated, and the inspection device body 30 completes the flaw detection inside the steel plate S in the divided region A1 of the front half. At this time, as illustrated in FIG. 11, a plurality of duplicate inspection avoidance regions B is provided. In each duplicate inspection avoidance region B, no inspection path is provided and only the movement path is provided to avoid the duplicate inspection by the flaw detection head 44 provided on the left side of the carriage 31 and the flaw detection head 44 provided on the right side of the carriage 31.

Then, when the flaw detection inside the steel plate S of the divided region A1 of the front half is completed, the two right and left wheels 32 are rotated forward and backward to rotate the inspection device body 30 180° (pivot turn), so that the detection heads 44 are directed to the side edge A2a side of the divided region A2 facing the above-described center line (straight line). Even when the flaw detection heads 44 detect flaws inside the steel plate S in the divided region A2 of the rear half while the flaw detection heads 44 are directed to the side edge A1a side of the divided region A1 without turning the inspection device body 30 180°, a region between the flaw detection heads 44 and the side edge A2a of the divided region A2 becomes a range where the inspection cannot be performed because the scanning actuator moving the flaw detection heads 44 is not provided.

Subsequently, in the divided region A2 of the rear half, the inspection device body 30 repeats an inspection path and a movement path constituting the movement route similar to those in the front half from the other end side in the longitudinal direction of the steel plate S (right end side of the steel plate S in FIG. 11) to one end side in the longitudinal direction of the steel plate S (left end side of the steel plate S in FIG. 11) in a state where the flaw detection heads 44 are directed to the side edge A2a side of the divided region A2 facing the center line (straight line). Thus, the inspection device body 30 detects flaws inside the steel plate S in the divided region A2 of the rear half. This makes it possible to inspect the entire inspection region having the rectangular shape of the surface Sa of the rectangular steel plate S as the inspection target. At this time, as with the divided region A1 of the front half, the plurality of duplicate inspection avoidance regions B is provided to avoid the duplication inspection by the flaw detection head 44 on the left side and the flaw detection head 44 on the right side.

Thus, as in the example of the inspection pattern according to JIS G0801: Ultrasonic testing of steel plates for pressure vessels illustrated in FIG. 12, the flaw detection inside the steel plate S is carried out at the inspection pitch D along the longitudinal direction of the steel plate S.

The inspection pitch D is about 20 mm, 100 mm, 200 mm, or 250 mm.

Then, as illustrated in FIG. 2, the inspection data obtained by the flaw detection heads 44 is transmitted to the setting/evaluation unit 15 of the on-board computer 36 via the ultrasonic flaw detector body 43 and the IO board 37 for evaluation.

As described above, according to the moving inspection device 20 of this embodiment, the inspection device body 30 includes: the carriage 31 moving by the two wheels 32 capable of rotating forward and backward in the forward and backward direction orthogonal to the rotation shafts 32a of the wheels 32 over the surface Sa of the steel plate S as the inspection target; and the flaw detection heads 44 as two inspection sensors arranged on the rear end side of the carriage 31 and inspecting the steel plate S for defects. The inspection region having the rectangular shape of the steel plate S is divided into the two divided regions A1, A2 formed in the rectangular shapes across the center line (straight line) and the carriage 31 of the inspection device body 30 move in the state where the flaw detection heads 44 are directed to the side edges A1a, A2a sides of the divided regions A1, A2 facing the center line (straight line) in each of the two divided regions A1, A2, respectively.

Thus, the steel plate S can be inspected by the moving inspection device body 30 using the drive of at least the two wheels 32 capable of rotating forward and backward, not turning each wheel 32, and not requiring the scanning actuator causing the flaw detection heads 44 to scan. Therefore, the moving inspection device 20 capable of appropriately inspecting the steel plate S as the inspection target while realizing the simplification of the configuration and significant size reduction/weight reduction of the device.

The movement route of the inspection device body 30 includes the inspection path and the movement path in each of the two divided regions A1, A2. In the inspection path, the steel plate S is inspected while the flaw detection heads 44 linearly move from the position on the center line (straight line) to the positions on the side edges A1a, A2a of the divided regions A1, A2, respectively. In the movement path, the flaw detection heads 44 move in the track containing the two curves R1, R2 from the positions on the side edges A1a, A2a of the divided regions A1, A2, respectively, to the other positions on the center line (straight line).

Thus, the steel plate S can be surely inspected for defects by the moving inspection device body 30 using the drive of at least the two wheels 32 capable of rotating forward and backward, not turning each wheel 32, and not requiring the scanning actuator causing the flaw detection heads 44 to scan.

Further, according to a moving inspection method of this embodiment, the steel plate S as the inspection target is inspected for defects using the above-described moving inspection device 20. Therefore, the steel plate S as the inspection target can be inspected for defects using the moving inspection device 20 capable of appropriately inspecting the steel plate S while realizing the simplification of the configuration and the significant size reduction/weight reduction of the device.

The steel plate S as a steel material is manufactured through an inspection step of implementing the moving inspection method.

The embodiments of the present invention are described above but the present invention is not limited thereto and can be variously altered or modified.

For example, the inspection target to be inspected by the moving inspection device 20 is not limited to the steel plate S.

The inspection target is not limited to the rectangular shape, the inspection region of the inspection target is not limited to the case of being formed in the rectangular shape, and each of the two divided regions A1, A2 is not limited to the case of being formed in the rectangular shape.

The inspection of the steel plate S for defects by the moving inspection device 20 may also include inspecting the steel plate S for all defects including internal defects of the steel plate S and surface defects of the front surface side and the rear surface side of the steel plate S without being limited to the inspection of the steel plate S for internal defects and surface defects of the rear surface side of the steel plate S by the ultrasonic flaw detection.

The inspection device body 30 is not limited to one having the structure illustrated in FIG. 1 and FIG. 3 to FIG. 5 and may be any one inspecting the steel plate S for defects while moving over the surface Sa of the steel plate S as the inspection target.

The pair of right and left wheels 32 capable of rotating forward and backward is provided but at least two wheels may be provided and three or four wheels may be acceptable.

The pair of right and left flaw detection heads 44 as the inspection sensors is installed but the number of the flaw detection heads 44 may be one or three or more.

The flaw detection heads as the inspection sensors are installed on the rear end side of the carriage 31 but may be installed on the front end side of the carriage 31. However, in this case, when the carriage 31 is moved over the surface Sa of the steel plate S, the flaw detection heads 44 are moved in a state of being directed to the side edges A1a, A2a sides of the two divided regions A1, A2 facing the center line (straight line) in each of the two divided regions A1, A2, respectively. More specifically, the carriage 31 is moved in a state where the front end side of the carriage 31 is directed to the side edges A1a, A2a of the divided regions A1, A2, respectively.

When the inspection region formed in the rectangular shape of the steel plate S is divided into the two divided regions A1, A2 formed in the rectangular shapes, the inspection region may be divided across a straight line at a position other than the center in the width direction of the steel plate S without being limited to the case where the inspection region is divided at the center line in the width direction of the steel plate S.

The movement path of the inspection device body 30 is designed such that the flaw detection heads 44 move in the track containing the two curves R1, R2 from the positions on the side edges A1a, A2a of the divided regions A1, A2, respectively, to the other positions on the center line (straight line). However, the track in this movement path may include a curve, and may be a track containing only one curve, may be a track containing two or more curves, or may be a track containing a curve and a straight line.

EXAMPLES

Figure 13:
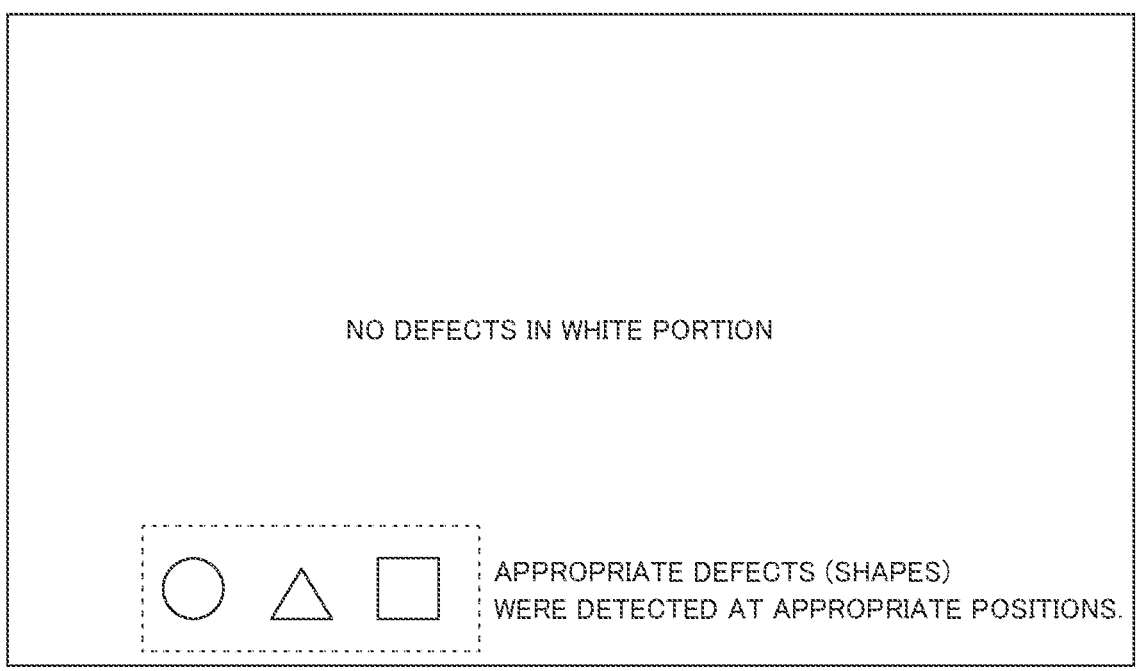
FIG. 13 is a view illustrating an inspection map when a steel plate as the inspection target was inspected for defects by a moving inspection device according to Examples.
Figure 14:
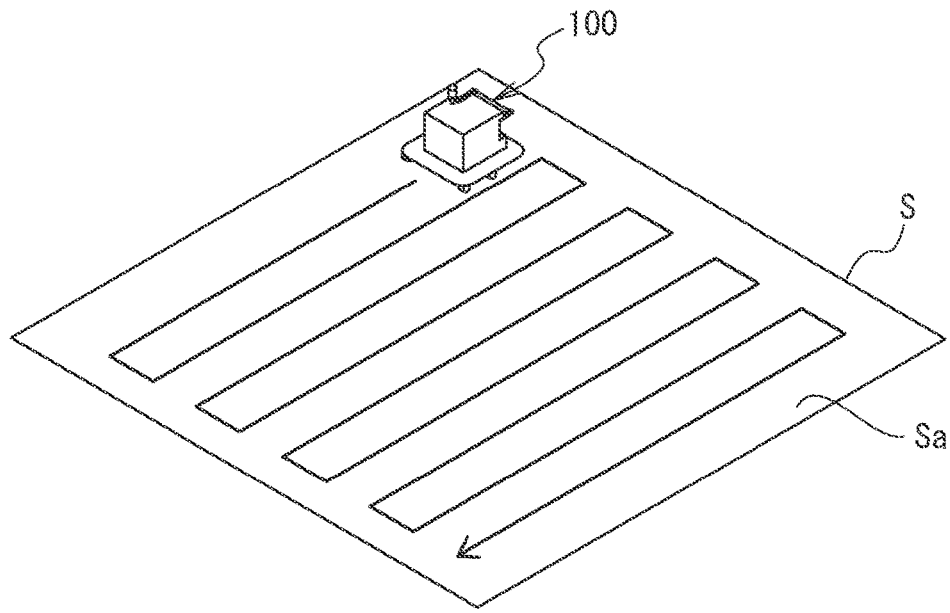
FIG. 14 is a view for explaining a typical movement route of a moving inspection device performing four-wheel drive/four-wheel steering.
Figure 15:
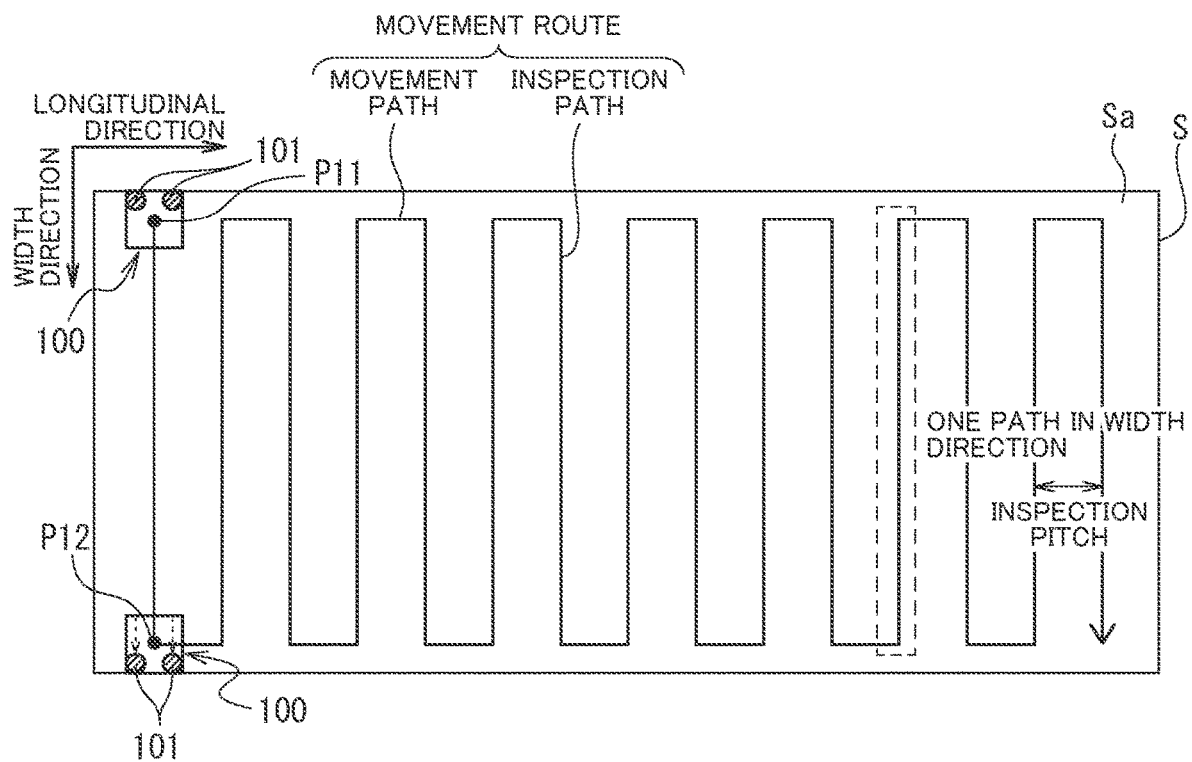
FIG. 15 is a view for explaining a specific movement route of the moving inspection device illustrated in FIG. 14 when inspecting the steel plate as the inspection target.

A steel plate provided with artificial defects (○, Δ, □) was inspected using the moving inspection device 20 illustrated in FIG. 1 as a moving inspection device according to Examples. An inspection map therefor is illustrated in FIG. 13. The inspection map was created by associating the position of the inspection device body 30 with inspection data at that position.

The positions and the shapes of the artificial defects (○, Δ, □) provided on the steel plate were accurately known in advance, and thus it was able to be confirmed that the inspection by the moving inspection device according to Examples had sufficient accuracy.

The mass of conventional moving inspection devices (moving inspection devices having a configuration similar to that illustrated in PTL 1 or PTL 2) is about 80 kg (exceeds 100 kg when filled with water) because a water tank was provided, and thus the conventional moving inspection devices were very heavy. Therefore, a lifter or the like was used in the movement between steel plates of the moving inspection devices, and thus there was room for improvement.

In contrast thereto, in the moving inspection device according to Examples, the water supply devices 80 were provided separately from the inspection device body 30 and the drive mechanism was innovated (four-wheel drive/four-wheel steering→two-wheel drive/non-steering). Therefore, the mass of the inspection device body 30 itself was reduced to about 20 kg, and, at the same time, the size was also able to be reduced. This enabled manual transportation, which significantly improved the handleability of the inspection device body 30. Further, the water supply devices 80 are very lightweight and may be manually installed on a steel plate for each inspection of the steel plate, and thus the handleability thereof does not matter.

REFERENCE SIGNS LIST

1 inspection system
10 indoor position measuring system
11 navigation transmitter
12 navigation receiver
13 current position calculation unit
14 position deviation calculation unit
15 setting/evaluation unit
16 drive control unit
20 moving inspection device
30 moving inspection device body
31 carriage
32 wheel (drive)
32a rotation shaft
32b first intersecting axis gears
33 wheel driving motor
33a output rotation shaft
33b second intersecting axis gears
34 wheel (omnidirectional)
35 control box
36 on-board computer
37 IO board
38 first raised part
39 second raised part
40 first plate member
41 second plate member
42 third plate member
43 ultrasonic flaw detector body
44 flaw detection head (inspection sensor)
50 follow-up mechanism
51 sensor holding mechanism
52 load adjustment mechanism
53a holder
53b sensor holding frame member
53c bolt
53d wing bolt
53e screw member
53f through hole
54 first support member
55 first hinge
56 second support member
57 second hinge
58 third support member
59 lower flat plate
60 upper flat plate
61 shaft
62 bush
62a flange
63 metal washer
64 metal washer
65 compression coil spring
66 metal washer
67 compression coil spring
68 nut
69 attachment plate
70 rail member
71 slider
72 attachment plate part
73 flow adjustment plate
73a first arc surface (arc surface)
73b second arc surface
74 flow adjustment plate attachment member
74a support leg part
74b arc-shaped attachment plate part
80 water supply device
81 nozzle
82 attachment plate
82a fixing member
83 attachment base
84 hose 85 joint
86 hose
91 actuator
92 distance meter
93 actuator control device
S steel plate (inspection target)
Sa surface
A1, A2 divided region
A1a, A2a side edge of divided region
B duplicate inspection avoidance region
D inspection pitch
W water

The invention claimed is:

1. A moving inspection device comprising:
a moving inspection device body configured to inspect an inspection target for a defect while moving over a surface of the inspection target, wherein
the moving inspection device body includes:
a carriage configured to move by at least two wheels capable of rotating forward and backward over the surface of the inspection target in a forward and backward direction orthogonal to rotation shafts of the wheels; and
at least one inspection sensor arranged on a front end side or a rear end side of the carriage and configured to inspect the inspection target for a defect,
an inspection region of the inspection target is divided into two divided regions across a straight line, and
the carriage of the moving inspection device body is configured to move in a state where the inspection sensor is directed to a side edge side of the divided region facing the straight line in each of the two divided regions.

2. The moving inspection device according to claim 1, wherein
the inspection target has a rectangular shape,
the inspection region is formed in a rectangular shape, and each of the two divided regions has a rectangular shape.

3. The moving inspection device according to claim 1, wherein
a movement route of the moving inspection device body includes in each of the two divided regions:
an inspection path where the inspection sensor inspects the inspection target while linearly moving from a position on the straight line to a position on the side edge of the divided region; and
a movement path where the inspection sensor moves in a track containing a curve from a position on the side edge of the divided region to a position on the straight line different from the position on the straight line.

4. A moving inspection method comprising:
inspecting an inspection target for a defect using the moving inspection device according to claim 1.

5. A method for manufacturing a steel material comprising:
an inspection step of implementing the moving inspection method according to claim 4.

6. The moving inspection device according to claim 2, wherein
a movement route of the moving inspection device body includes in each of the two divided regions:
an inspection path where the inspection sensor inspects the inspection target while linearly moving from a position on the straight line to a position on the side edge of the divided region; and
a movement path where the inspection sensor moves in a track containing a curve from a position on the side edge of the divided region to a position on the straight line different from the position on the straight line.

7. A moving inspection method comprising:
inspecting an inspection target for a defect using the moving inspection device according to claim 2.

8. A moving inspection method comprising:
inspecting an inspection target for a defect using the moving inspection device according to claim 3.

9. A method for manufacturing a steel material comprising:
an inspection step of implementing the moving inspection method according to claim 7.

10. A method for manufacturing a steel material comprising:
an inspection step of implementing the moving inspection method according to claim 8.

* * * * *